(12) United States Patent
Gagner

(10) Patent No.: US 12,396,874 B2
(45) Date of Patent: Aug. 26, 2025

(54) MAGNETIC DEVICES FOR DIGESTIVE TRACT PARTITIONING

(71) Applicant: GT Metabolic Solutions, Inc., Wilmington, DE (US)

(72) Inventor: Michel Gagner, Montreal (CA)

(73) Assignee: GT Metabolic Solutions, Inc., Wilmington, DE (US)

( * ) Notice: Subject to any disclaimer, the term of this patent is extended or adjusted under 35 U.S.C. 154(b) by 314 days.

(21) Appl. No.: 17/919,137

(22) PCT Filed: Jan. 28, 2021

(86) PCT No.: PCT/CA2021/050086
§ 371 (c)(1),
(2) Date: Oct. 14, 2022

(87) PCT Pub. No.: WO2021/207821
PCT Pub. Date: Oct. 21, 2021

(65) Prior Publication Data
US 2023/0157856 A1 May 25, 2023

Related U.S. Application Data

(60) Provisional application No. 63/011,691, filed on Apr. 17, 2020.

(51) Int. Cl.
*A61F 5/00* (2006.01)
*A61B 17/00* (2006.01)
*A61B 17/122* (2006.01)

(52) U.S. Cl.
CPC .......... *A61F 5/0086* (2013.01); *A61B 17/122* (2013.01); *A61B 2017/00876* (2013.01)

(58) Field of Classification Search
CPC ............ A61B 17/12009; A61B 17/122; A61B 2017/00876; A61F 5/0086
(Continued)

(56) References Cited

U.S. PATENT DOCUMENTS

| 8,591,396 B2 | 11/2013 | Zemlok et al. |
| 8,870,898 B2 | 10/2014 | Beisel et al. |
| (Continued) | | |

FOREIGN PATENT DOCUMENTS

| WO | 2009029228 A2 | 3/2009 |
| WO | 2013028390 A1 | 2/2013 |
| (Continued) | | |

OTHER PUBLICATIONS

European Patent Office—Extended European Search Report, pertaining to European Patent Application No. 21789350.2 dated Mar. 19, 2024, 8 pages.
(Continued)

*Primary Examiner* — Jocelin C Tanner
(74) *Attorney, Agent, or Firm* — Sunstein LLP

(57) ABSTRACT

There is provided a partitioning device to partition a hollow organ of a digestive tract of a patient in the context of digestive surgeries. The partitioning device includes a magnet assembly implantable into an abdominal cavity of the patient, the magnet assembly including a plurality of magnet elements flexibly connected in series. The magnet assembly is configured to be positioned extraluminally around at least a portion of an outer surface of the hollow organ to magnetically couple opposite magnet elements together to compress opposite walls of the hollow organ therebetween until opposite walls of the hollow organ are fused together, thereby partitioning the hollow organ. The magnet elements can be received in a housing and have various shapes. The partitioning device can include additional features such as a leading elongated member that can aid in the positioning of the partitioning device, and a trailing elongated member.

20 Claims, 18 Drawing Sheets

(58) Field of Classification Search
USPC .......................................................... 606/157
See application file for complete search history.

(56) References Cited

U.S. PATENT DOCUMENTS

| | | | |
|---|---|---|---|
| 2009/0163937 A1 | 6/2009 | Kassab et al. | |
| 2010/0280304 A1 | 11/2010 | Zemlok et al. | |
| 2010/0318015 A1 | 12/2010 | Kassab et al. | |
| 2012/0095484 A1* | 4/2012 | Dominguez | A61F 5/0036 606/157 |
| 2012/0150214 A1 | 6/2012 | Kugler et al. | |
| 2015/0164508 A1* | 6/2015 | Hernandez | A61B 17/1114 606/153 |
| 2016/0022266 A1 | 1/2016 | Lukin et al. | |
| 2016/0058594 A1* | 3/2016 | Armenteros | A61B 17/1285 600/37 |
| 2016/0324523 A1* | 11/2016 | Lukin | A61B 17/1114 |
| 2016/0324527 A1* | 11/2016 | Thompson | A61B 17/068 |
| 2018/0008447 A1 | 1/2018 | Jacobs et al. | |
| 2019/0183507 A1* | 6/2019 | Baillargeon | A61B 17/1114 |
| 2019/0209175 A1 | 7/2019 | Thompson et al. | |
| 2019/0224029 A1 | 7/2019 | Thompson et al. | |
| 2019/0274689 A1 | 9/2019 | Auld et al. | |

FOREIGN PATENT DOCUMENTS

| | | |
|---|---|---|
| WO | 2016183039 A1 | 11/2016 |
| WO | 2018009669 A1 | 1/2018 |

OTHER PUBLICATIONS

International Searching Authority—International Search Report, pertaining to International Application No. PCT/CA2021/050086 dated Apr. 23, 2021, together with the Written Opinion of the International Searching Authority, 10 pages.

* cited by examiner

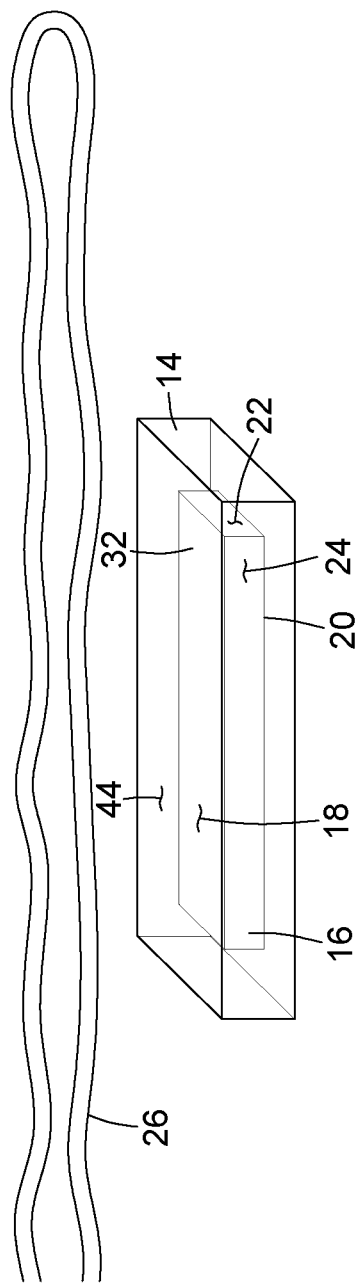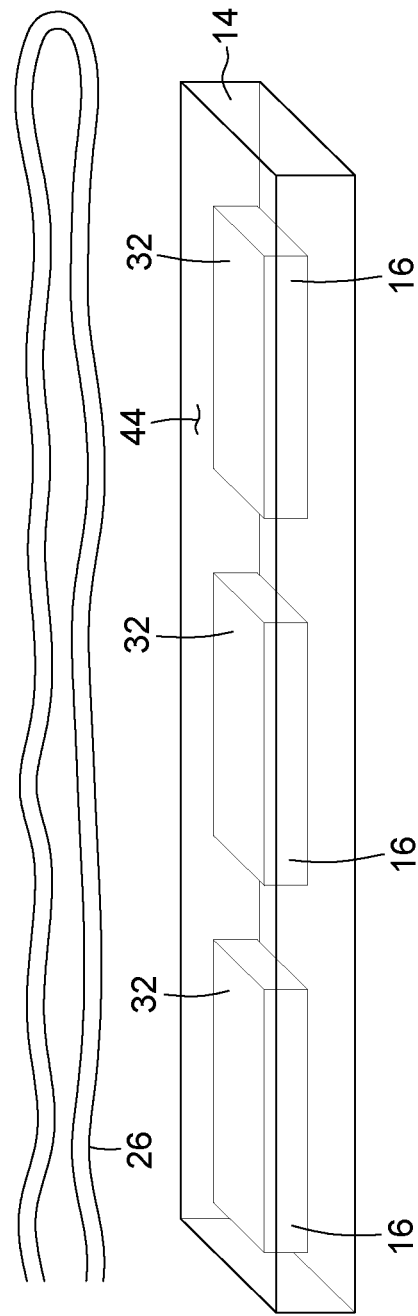

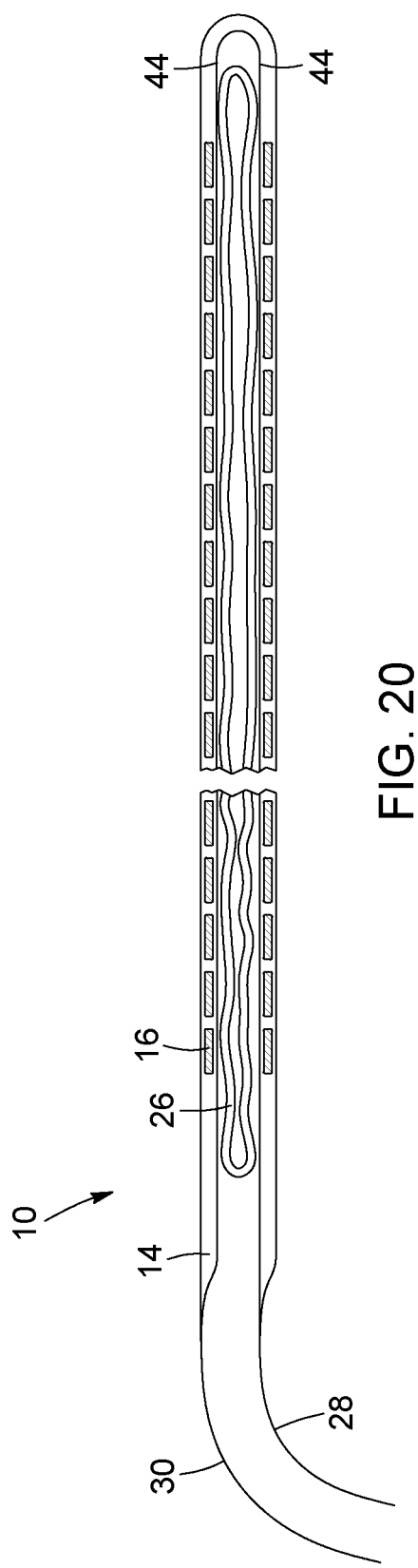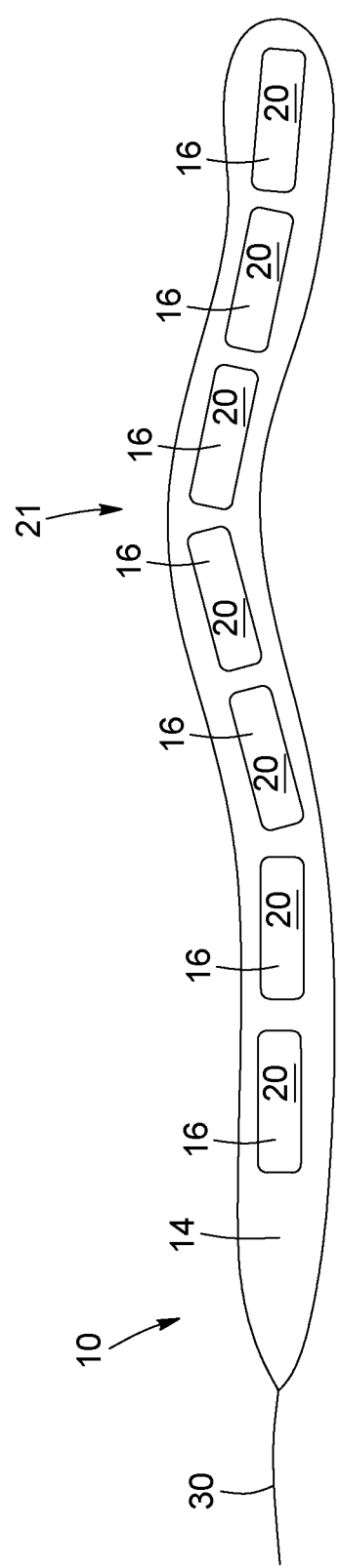

MAGNETIC DEVICES FOR DIGESTIVE TRACT PARTITIONING

CROSS-REFERENCE TO RELATED APPLICATIONS

This application is the national stage entry under 35 U.S.C. § 371 of International Patent Application No. PCT/CA2021/050086 filed on Jan. 28, 2021, and claims the benefit of U.S. Provisional Patent Application No. 63/011,691 filed Apr. 17, 2020, the disclosures of which are incorporated herein by reference in their entirety.

TECHNICAL FIELD

The technical field generally relates to medical techniques for treating digestive tract conditions. In particular, the technical field relates to medical techniques for partitioning a hollow organ of the digestive tract.

BACKGROUND

Bariatric surgery procedures can be used to treat obesity, and are generally aimed at restricting the size of an organ such as the stomach, and/or bypassing a portion of the stomach and/or the intestine. Examples of bariatric surgery procedures can include jejuno-ileal bypass, jejuno-colic shunt, biliopancreatic diversion, gastric bypass, Roux-en-Y gastric bypass, gastroplasty, gastric banding, vertical banded gastroplasty, silastic ring gastroplasty, and sleeve gastrectomy.

However, these bariatric surgery procedures often require alteration of the digestive tract through incisions, sutures, punctures and/or stapling, which can cause trauma to the organ being altered and lead to bleeding. Such bariatric surgery procedures can also lead to an increased risk of infection or other complications.

Accordingly, there remain a number of challenges with respect to bariatric surgery procedures.

SUMMARY

In accordance with an aspect, there is provided a method for partitioning a hollow organ of a digestive tract of a patient, the method comprising the steps of:
  inserting a magnet assembly of a partitioning device into an abdominal cavity of the patient, the magnet assembly comprising a plurality of magnet elements flexibly connected in series;
  positioning the magnet assembly extraluminally around at least a portion of an outer surface of the hollow organ and along a partitioning line such that an anterior portion of the magnet assembly and a posterior portion of the magnet assembly face each other;
  magnetically coupling opposite magnet elements together to compress opposite walls of the hollow organ therebetween; and
  allowing the opposite walls of the hollow organ to fuse together while the magnet elements remain magnetically coupled.

In some implementations, the partitioning device further comprises a first end and a second end with the magnet assembly extending between the first end and the second end.

In some implementations, the magnet assembly comprises a first zone and a second zone, and inserting the magnet assembly of the partitioning device into the abdominal cavity of the patient comprises inserting the first zone of the magnet assembly first followed by the second zone of the magnet assembly.

In some implementations, positioning the magnet assembly extraluminally around the at least a portion of the outer surface of the hollow organ and along the partitioning line comprises positioning the first zone of the magnet assembly as the posterior portion of the magnet assembly and positioning the second zone of the magnet assembly as the anterior portion of the magnet assembly.

In some implementations, each one of the magnet elements comprises a magnet-engaging side, and magnetically coupling opposite magnet elements together comprises magnetically coupling opposite magnet-engaging sides of the magnet elements facing each other.

In some implementations, the magnet-engaging sides of the magnet elements of the first zone of the magnet assembly have a first zone magnetic pole, and the magnet-engaging sides of the magnet elements of the second zone of the magnet assembly have a second zone magnetic pole that is different from the first zone magnetic pole.

In some implementations, magnetically coupling opposite magnet elements together comprises magnetically coupling the first zone magnetic pole of the magnet-engaging sides of the magnet elements of the first zone with the second zone magnetic pole of the magnet-engaging sides of the magnet elements of the second zone.

In some implementations, allowing the opposite walls of the hollow organ to fuse together while the magnet elements remain magnetically coupled comprises leaving the magnet assembly along the partition line for a given period of time.

In some implementations, the given period of time ranges from about 1 week to about 7 weeks.

In some implementations, the method further comprises removing the partitioning device from the abdominal cavity of the patient once the opposite walls of the hollow organ are fused together.

In accordance with another aspect, there is provided a method for partitioning a hollow organ of a digestive tract of a patient, the method comprising the steps of:
  inserting a leading elongated member and a magnet assembly of a partitioning device into an abdominal cavity of the patient, the leading elongated member extending from a leading end of the magnet assembly and the magnet assembly comprising a plurality of magnet elements flexibly connected in series;
  guiding the leading elongated member to position the magnet assembly extraluminally around at least a portion of an outer surface of the hollow organ such that an anterior portion of the magnet assembly and a posterior portion of the magnet assembly face each other;
  magnetically coupling opposite magnet elements along a partitioning line to compress opposite walls of the hollow organ therebetween;
  allowing the opposite walls of the hollow organ to fuse together while the magnet elements are magnetically coupled together.

In some implementations, guiding the leading elongated member comprises engaging the leading elongated member with a delivery catheter and laparoscopically guiding the leading elongated member around the at least a portion of the outer surface of the hollow organ.

In some implementations, the leading elongated member is configured to remain at a subcutaneous location while the opposite walls of the hollow organ fuse together.

In some implementations, the partitioning device further comprises a trailing elongated member extending from a trailing end of the magnet assembly, the trailing elongated member being configured to remain subcutaneously or outside the patient while the opposite walls of the hollow organ fuse together.

In some implementations, the method further comprises removing the partitioning device from the abdominal cavity of the patient once the opposite walls of the hollow organ are fused together.

In some implementations, removing the partitioning device comprises pulling on one of the leading elongated member and the trailing elongated member to extract the partitioning device out of the abdominal cavity of the patient.

In accordance with another aspect, there is provided a method for partitioning a hollow organ of a digestive tract of a patient, the method comprising the steps of:
  inserting a magnet assembly of a partitioning device into an abdominal cavity of the patient, the magnet assembly comprising:
    a plurality of magnet elements flexibly connected in series;
    a housing comprising an organ-contacting side and being configured to receive the plurality of magnet elements therein;
  positioning the magnet assembly extraluminally around at least a portion of an outer surface of the hollow organ and along a partitioning line such that an anterior portion of the organ-contacting side and a posterior portion of the organ-contacting side face each other;
  magnetically coupling opposite magnet elements together to compress opposite walls of the hollow organ between the anterior and the posterior portions of the organ-contacting side of the housing; and
  allowing the opposite walls of the hollow organ to fuse together while the magnet elements remain magnetically coupled.

In some implementations, the organ-contacting side of the housing comprises an elongated flat contact surface.

In some implementations, the housing comprises bevelled edges.

In accordance with another aspect, there is provided a method for partitioning a hollow organ of a digestive tract of a patient, the method comprising the steps of:
  inserting a magnet assembly of a partitioning device into an abdominal cavity of the patient, the magnet assembly comprising:
    a plurality of magnet elements flexibly connected in series, each one of the plurality of magnet elements being received in a corresponding housing comprising an organ-contacting side;
  positioning the magnet assembly extraluminally around at least a portion of an outer surface of the hollow organ and along a partitioning line such that an anterior portion of the organ-contacting side and a posterior portion of the organ-contacting side face each other;
  magnetically coupling opposite magnet elements together to compress opposite walls of the hollow organ between the anterior and the posterior portions of the organ-contacting side of the housing; and
  allowing the opposite walls of the hollow organ to fuse together while the magnet elements remain magnetically coupled.

In some implementations, the organ-contacting side of the housing comprises an elongated flat contact surface.

In some implementations, the housing comprises bevelled edges.

In accordance with another aspect, there is provided a partitioning device to partition a hollow organ of a digestive tract of a patient, the partitioning device comprising:
  a magnet assembly implantable into an abdominal cavity of the patient and comprising:
    a plurality of magnet elements flexibly connected in series;
  wherein the magnet assembly is configured to be positioned extraluminally around at least a portion of an outer surface of the hollow organ to magnetically couple opposite magnet elements together to compress opposite walls of the hollow organ therebetween until opposite walls of the hollow organ are fused together, thereby partitioning the hollow organ.

In some implementations, the partitioning device further comprises a leading elongated member and a trailing elongated member, with the magnet assembly extending therebetween.

In some implementations, the leading elongated member is configured for engagement with a delivery catheter to guide the magnet assembly to the hollow organ and around the at least a portion of the outer surface thereof.

In some implementations, each one of the magnet elements comprises a magnet-engaging side to magnetically couple opposite magnet-engaging sides of the magnet elements facing each other.

In some implementations, the magnet assembly comprises a first zone and a second zone, the magnet-engaging sides of the magnet elements of the first zone of the magnet assembly having a first zone magnetic pole, and the magnet-engaging sides of the magnet elements of the second zone of the magnet assembly having a second zone magnetic pole that is different from the first zone magnetic pole.

In some implementations, the magnet elements have a shape selected from the group consisting of an oblong shape, a stadium shape, a circular shape, a triangular shape, a rectangular shape, and an octagonal shape.

In some implementations, the magnet elements comprise bevelled edges.

In some implementations, the magnet elements comprise rounded edges.

In some implementations, the magnet-engaging side of the magnet elements have a smaller surface area compared to a side of the magnet element located opposite the magnet-engaging side.

In some implementations, the magnet elements are flexibly connected in series via a flexible connector.

In some implementations, the flexible connector comprises a flexible string.

In some implementations, the partitioning device is configurable between a pre-partitioning configuration and a partitioning configuration.

In some implementations, the partitioning device comprises a curved region.

In some implementations, an attractive force of the magnet element is determined at least in part in accordance with a thickness and/or a composition of the hollow organ.

In some implementations, an attractive force of the magnet elements is determined so as to facilitate placement and implantation of the partitioning device around the portion of the outer surface of the hollow organ.

In some implementations, the plurality of magnet elements flexibly connected in series are provided in sufficiently close proximity to enable formation of a substantially continuous partition line once opposite walls of the hollow organ are fused together.

In some implementations, the magnet elements are received in a housing.

In some implementations, each one the magnet elements is received in a corresponding housing.

In some implementations, the housing comprises bevelled edges.

In some implementations, the corresponding housing comprises bevelled edges.

In accordance with another aspect, there is provided a partitioning device to partition a hollow organ of a digestive tract of a patient, the partitioning device comprising:
 a leading elongated member and a trailing elongated member; and
 a magnet assembly extending between the leading elongated member and the trailing elongated member, the magnet assembly being implantable into an abdominal cavity of the patient and comprising:
  a plurality of magnet elements flexibly connected in series;
wherein the magnet assembly is configured to be positioned extraluminally around at least a portion of an outer surface of the hollow organ by guiding the leading elongated member of the partitioning device to magnetically couple opposite magnet elements together to compress opposite walls of the hollow organ therebetween until opposite walls of the hollow organ are fused together, thereby partitioning the hollow organ.

In some implementations, the leading elongated member is a flexible leading elongated member.

In some implementations, the flexible leading elongated member comprises at least one of a flexible cord and a flexible wire.

In some implementations, the leading elongated member is configured for engagement with a delivery catheter.

In some implementations, at least one of the leading elongated member and the trailing elongated member is configured to anchor the partitioning device subcutaneously or outside the patient while opposite walls of the hollow organ are compressed between opposite magnet elements.

In some implementations, the partitioning device is configurable between a pre-partitioning configuration and a partitioning configuration.

In some implementations, in the partitioning configuration, the leading elongated member and the trailing elongated member are in proximity of each other for the partitioning device to form a partial loop or a loop.

In some implementations, the leading elongated member and the trailing elongated member comprises a continuous elongated member configured to be slidably engageable with the magnet assembly.

In accordance with another aspect, there is provided a partitioning device to partition a hollow organ of a digestive tract of a patient, the partitioning device comprising:
 a magnet assembly comprising:
  a plurality of magnet elements flexibly connected in series;
  a housing configured to receive the plurality of magnet elements therein and comprising an organ-contacting side;
wherein the magnet assembly is configured to be positioned extraluminally around at least a portion of an outer surface of the hollow organ to magnetically couple opposite magnet elements together to compress and fuse together opposite walls of the hollow organ between opposite organ-contacting sides of the housing.

In some implementations, the organ-contacting side of the housing comprises an elongated flat contact surface.

In some implementations, the housing has a shape selected from the group consisting of an oblong shape, a stadium shape, a circular shape, a triangular shape, a rectangular shape, and an octagonal shape.

In some implementations, the housing comprises bevelled edges.

In some implementations, the housing comprises rounded edges.

In some implementations, the organ-contacting side of the housing has a smaller surface area compared to a side of the housing located opposite the organ-contacting side.

In some implementations, the magnet elements are flexibly connected in series via a flexible connector.

In some implementations, the housing comprises a plurality of housings, each one of the magnet elements being received in a corresponding one of the plurality of housings.

In some implementations, the flexible connector is provided between adjacent ones of the plurality of housings.

In some implementations, the housing comprises a connecting portion between adjacent ones of the plurality of housings to flexibly connect together adjacent magnet elements of the plurality of magnet elements.

In some implementations, the housing receiving the plurality of magnet elements therein is a single housing.

In some implementations, the flexible connector is provided within the single housing.

In some implementations, the housing comprises metal.

In some implementations, the metal comprises at least one of stainless steel, titanium, and a medical implant grade metals.

In some implementations, the housing comprises a polymer.

In some implementations, the polymer comprises at least one of silicone, Silastic™ and a medical implant grade polymers.

In accordance with another aspect, there is provided a partitioning device to partition a hollow organ of a digestive tract, the partitioning device comprising:
 a magnet assembly implantable into an abdominal cavity of a patient and comprising:
  a plurality of magnet elements flexibly connected in series, each one of the magnet elements having a magnet-engaging side;
  a flexible housing configured to receive the plurality of magnet elements therein, the housing comprising an organ-contacting side;
wherein the device is configurable in a pre-partitioning configuration for insertion into the abdominal cavity and in a partitioning configuration for partitioning the hollow organ;
wherein in the pre-partitioning configuration, the magnet-engaging sides of the magnet elements are magnetically uncoupled to each other, and in the partitioning configuration, the magnet assembly forms a U-shape around the hollow organ to magnetically couple opposite magnet-engaging sides and compress and fuse together opposite walls of the hollow organ between opposite sections of the elongated flat contact surface of the housing.

In some implementations, the pre-partitioning configuration comprises an extended pre-partitioning configuration.

In some implementations, the pre-partitioning configuration comprises a looped pre-partitioning configuration.

BRIEF DESCRIPTION OF THE DRAWINGS

FIG. 11 is a perspective view schematic of a magnet element shown in an arbitrary spatial relationship relative to walls of a portion of a hollow organ, the magnet element being received in a corresponding housing.

FIG. 12 is a perspective view schematic of three magnet elements of a portion of a magnet assembly shown in an arbitrary spatial relationship relative to walls of a portion of a hollow organ, the magnet elements being received in a single housing.

FIG. 20 is a side cross-sectional view schematic of a partitioning device that includes magnet elements received in a housing having an elongated flat contact surface on an organ-contacting side thereof, the partitioning device being shown in a partitioning configuration with walls of a hollow organ being compressed between the elongated flat contact surfaces.

FIG. 21 is a top view schematic of a partitioning device that includes magnet elements, the magnet elements being arranged to provide a curved region along the length of the portioning device.

DETAILED DESCRIPTION

Figure 1:
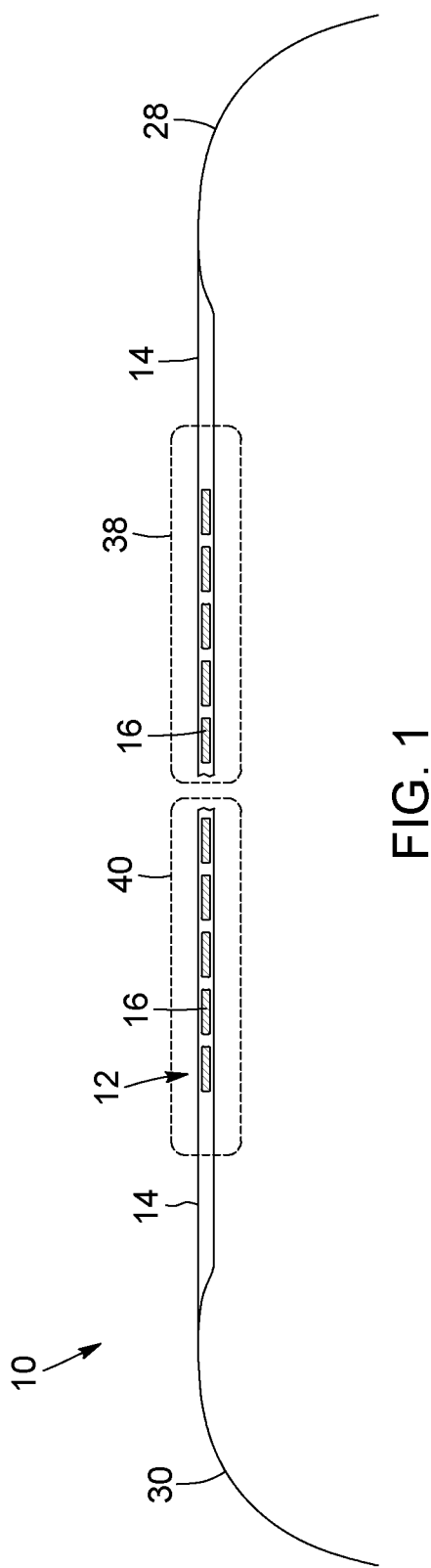
FIG. 1 is a side cross-sectional view schematic of a portion of a partitioning device that includes a magnet assembly having a first zone and a second zone, the partitioning device being shown in an extended pre-partitioning configuration.

Surgical procedures to treat various medical conditions associated with the digestive tract can include modifying the configuration of a hollow organ, such as the esophagus, stomach, gallbladder, a duct of the biliary system, small intestine, colon or rectum, or reducing the size of the lumen of such organs. Such surgical procedures can be performed for any surgery related to the digestive system, which can include bariatric surgeries, other digestive surgeries such as those that can be performed for instance in the context of a cancer treatment, resection surgeries, etc. Modifying the configuration or reducing the size of the lumen of an hollow organ can include partitioning the hollow organ into distinct sections by fusing together opposite walls of the organ, without puncturing the tissue. In order to do so, a method for partitioning a hollow organ of the digestive tract without puncturing the tissue can be implemented using a partitioning device. The partitioning device may include various features. It is to be understood that as used herein, the expression "partitioning device" can be used interchangeably with the expression "partitioning implant" throughout the present description, as the partitioning device is configured to be implanted and remain a certain period of time, which can extend from days to weeks, within the abdominal cavity of the patient.

The partitioning device can include a flexible magnet assembly that can be inserted into the abdominal cavity of the patient and positioned extraluminally around a portion of the outer surface of a target hollow organ. The flexibility of the magnet assembly can be conferred by flexibly connecting a series of magnet elements together to form a train of magnet elements. Each one of the magnet elements includes a respective magnet-engaging side, and consecutive ones of magnet elements have their respective magnet-engaging side on the same side. In some implementations, one or more magnet elements can be received in a respective housing, or the series of magnet elements can be received together in a single housing.

The partitioning device can be configured to adopt a pre-partitioning configuration and a partitioning configuration. The pre-partitioning configuration can facilitate the insertion of the partitioning device into an abdominal cavity of a patient, for instance in the context of a laparoscopy procedure, and subsequent placement around a target hollow organ. On the other hand, the partitioning configuration is a configuration that can enable the partitioning of the hollow organ.

In the pre-partitioning configuration, the magnet-engaging sides of the plurality of magnets are magnetically uncoupled to each other. To achieve such a pre-partitioning configuration, the magnet assembly extends longitudinally such that the magnet-engaging sides are not facing each other and can be inserted into the abdominal cavity longitudinally, e.g., as a string. This type of pre-partitioning configuration can be referred to as an extended pre-partitioning configuration. In another example of pre-partitioning configuration, the magnet assembly can form a U-shape to obtain a partial or closed loop with opposite magnet-engaging sides of the magnet elements facing each other, but being far enough from each other that the opposite magnet-engaging sides of the magnet elements remain magnetically uncoupled so as to allow the partial or closed loop to be placed around a target hollow organ. This pre-partitioning configuration can be referred to as a looped pre-partitioning configuration.

The choice of pre-partitioning configuration can depend on the target hollow organ around which the magnet assembly will be placed, and can take into consideration the space available around the target hollow organ. If the magnet assembly is initially inserted as a string, the pre-configuration will eventually include the formation of the U-shape for placement around the target hollow organ while the magnet elements remain magnetically uncoupled. In addition to facilitating the insertion of the partitioning device into the abdominal cavity, the pre-partitioning configuration can facilitate placement of the magnet assembly extraluminally around the outer surface of the hollow target hollow organ along a given partition line. In the context of the present description, the partition line corresponds to a delimitation between two portions of a target hollow organ, and thus to a tracing where the magnet-engaging sides of the magnet assembly of the partitioning are placed against to partition the target hollow organ.

Once the partitioning device is placed around the outer surface of the hollow organ, the magnet assembly can be placed in the partitioning configuration. In the partitioning configuration, opposite magnet elements on each side of the target hollow organ are placed in sufficiently close proximity so that opposite magnet-engaging sides of the magnet elements facing each other are magnetically coupled to bring together and compress the walls of the target hollow organ therebetween, without having to puncture the tissue of the organ. The magnetic coupling maintains the magnet elements in place, and the pressure applied by the magnet elements on the walls of the target hollow organ triggers a healing mechanism that over time, can lead to the fusion of the walls of the organ along the edges of the magnet elements. In the context of the present description, the term "fusion" can be interpreted as corresponding to the resulting healed tissue on the edges of the magnet elements that are now joined to form a single structure. The two opposite walls of the organ that were initially compressed between the magnet-engaging sides are eventually subjected to ischemic pressure necrosis, and after a certain period of time, which can extend from days to weeks, a space corresponding substantially to the width of the magnet elements will end up being defined between portions of the hollow organ.

The partitioning device is configured to remain in the abdominal cavity of the patient for a period of time that is sufficient to allow the healing process to take place and for the fusion of the walls of the organ on the edges the magnet elements to occur. Monitoring of the healing process can be advantageous to determine at which moment it may be advisable to remove the partitioning device out of the abdominal cavity of the patient after the fusion of the tissues has occurred.

The partitioning device can also include additional features. For instance, the partitioning device can include one or more features that can contribute to aid in the placement of the magnet assembly within the abdominal cavity. Such features can include a flexible elongated member, such as a flexible cord or a flexible wire, that is configured to extend from one extremity of the magnet assembly and that can also be referred to as leading elongated member. The flexible elongated member can be configured for engagement with a delivery catheter, and in turn, the delivery catheter can be used to carry and navigate the magnet assembly via the leading elongated member into the abdominal cavity, and around the target hollow organ.

Optionally, the partitioning device can also include a second flexible elongated member at the other extremity of the magnet assembly, opposite the leading elongated member, and this second flexible elongated member can be referred to as trailing elongated member. The trailing elongated member can be useful during implantation of the magnet assembly if a contact with the magnet assembly from outside of the patient is desired. Either one of the leading elongated member and the trailing elongated member, or both of them, can also be useful to anchor the partitioning device subcutaneously or outside the patient during the healing period.

Various implementations of the partitioning device and associated methods will now be described in greater detail.

Magnet Assembly

Magnet Elements

Figure 2:
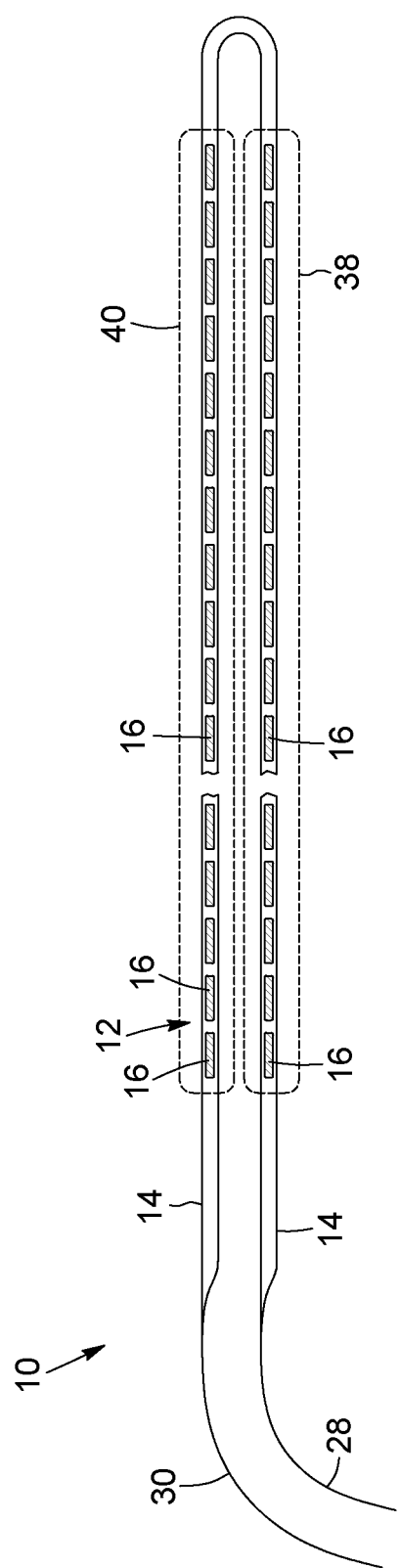
FIG. 2 is a side cross-sectional view schematic of a portion of a partitioning device that includes a magnet assembly having a first zone and a second zone, the partitioning device being shown in a looped pre-partitioning configuration.
Figure 3:
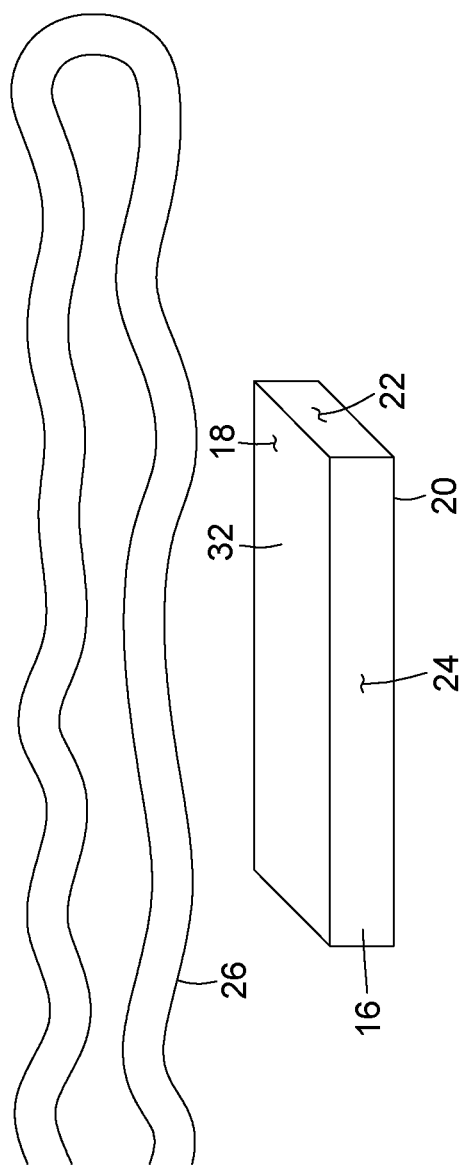
FIG. 3 is a perspective view schematic of a magnet element in an arbitrary spatial relationship with walls of a portion of a hollow organ.

With reference to FIGS. 1-3, an implementation of a partitioning device 10 is shown. The partitioning device 10 includes a magnet assembly 12 that is received in a housing 14. The magnet assembly 12 includes a plurality of magnet elements 16 that are connected together, or joined, in a flexible manner. The magnet element 16 includes a top side 18, a bottom side 20, lateral sides 22 and longitudinal sides 24. In the context of the present description, the top side 18 of the magnet element 16 refers to the side that faces the wall 26 of the target hollow organ once the magnet assembly 12 is implanted in the patient and placed around the outer surface of the target hollow organ. In the implementation shown, the partitioning device 10 further includes a flexible elongated member at each extremity, i.e., a leading elongated member 28 and a trailing elongated member 30. In addition, the housing 14 in which the magnet elements 16 are received is also flexible.

In FIG. 1, the partitioning device 10 is in a pre-partitioning configuration, where the partitioning device 10 is extended longitudinally such that the extremities of the magnet assembly 12 are spaced apart and opposite to each other. This type of pre-partitioning configuration can be referred to as an extended pre-partitioning configuration. In FIG. 2, the partitioning device 10 is also in a pre-partitioning configuration, albeit one that can be referred to as a looped pre-partitioning configuration. In the looped pre-partitioning configuration, the magnet assembly 12 is folded on itself in a U-shape to form a partial or closed loop, depending on the intended application. The choice of the pre-partitioning configuration for the magnet assembly 12 can depend on the hollow organ that is targeted to treat, and the choice of insertion method that is considered. As mentioned above, if the magnet assembly 12 is initially inserted as a string such as in shown in FIG. 1, the pre-partitioning configuration eventually includes the formation of the U-shape in a partial or closed loop for placement around the target hollow organ while the magnet elements 16 remain magnetically uncoupled. In other words, one of the characteristics of the pre-partitioning configuration of the magnet assembly 12 is that the magnet elements 16 are magnetically uncoupled, and the magnet assembly 12 can adopt various configurations where the magnet elements 16 are magnetically uncoupled. In addition to facilitating the insertion of the partitioning device 10 into the abdominal cavity, the pre-partitioning configuration can also facilitate placement of the magnet assembly 12 extraluminally around the outer surface of the target hollow organ along a given partition line 42. Additional details regarding these considerations are provided below.

The magnet elements 16 of the magnet assembly 12 can be any type of suitable magnet. In some implementations, the magnet elements 16 can be chosen according to their attractive force, i.e., according to the pressure that will be exerted on the surface area of the tissue that will eventually be compressed between magnetically coupled magnet elements 16. Factors influencing the attractive force of the magnet element 16 can include the shape of the magnet element 16, the thickness of the magnet element 16, the material that the magnet element 16 is made of, etc. Examples of materials can include neodymium magnets (e.g., NdFeB magnets), rare earth magnets and ferrite magnets.

Figure 4:
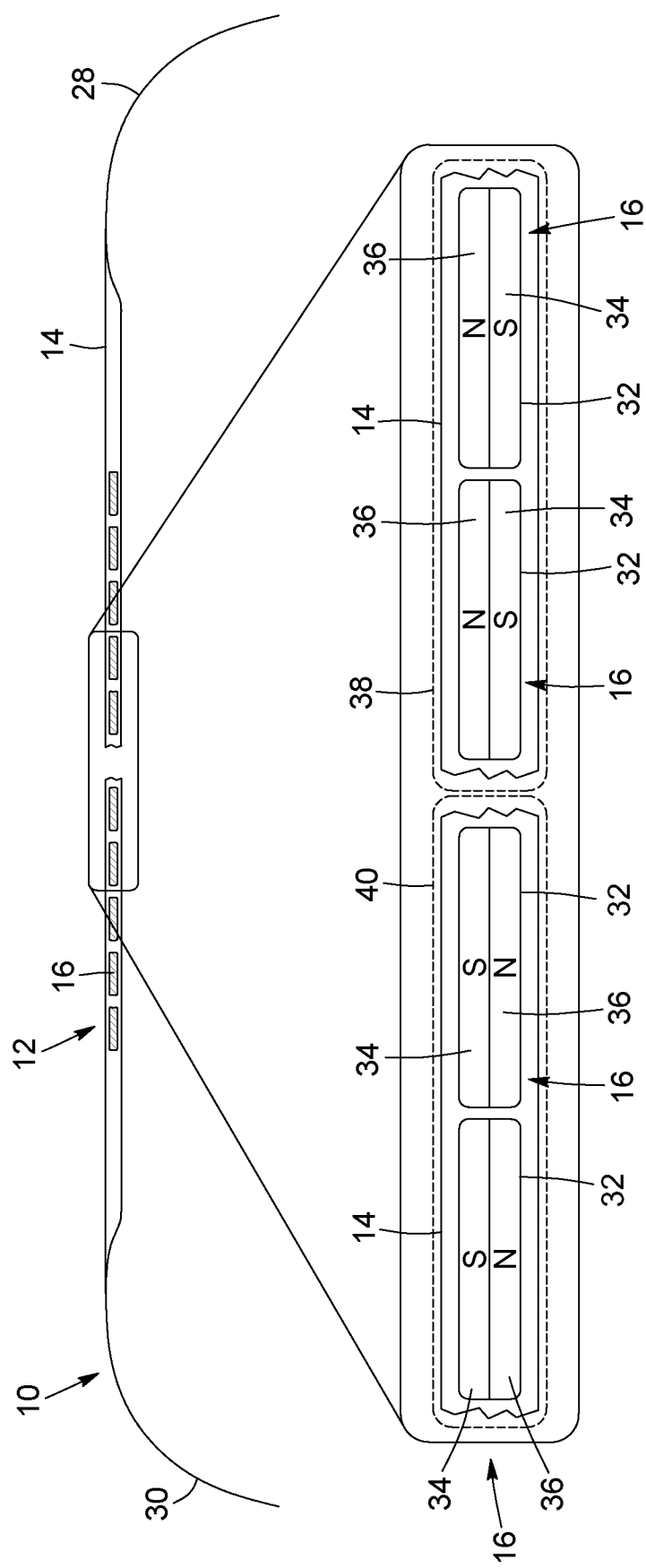
FIG. 4 is a side cross-sectional view schematic of a partitioning device in an extended pre-partitioning configuration, with an enlarged view of magnet elements in a first zone of a magnet assembly and magnet elements in a second zone of the magnet assembly.
Figure 5:
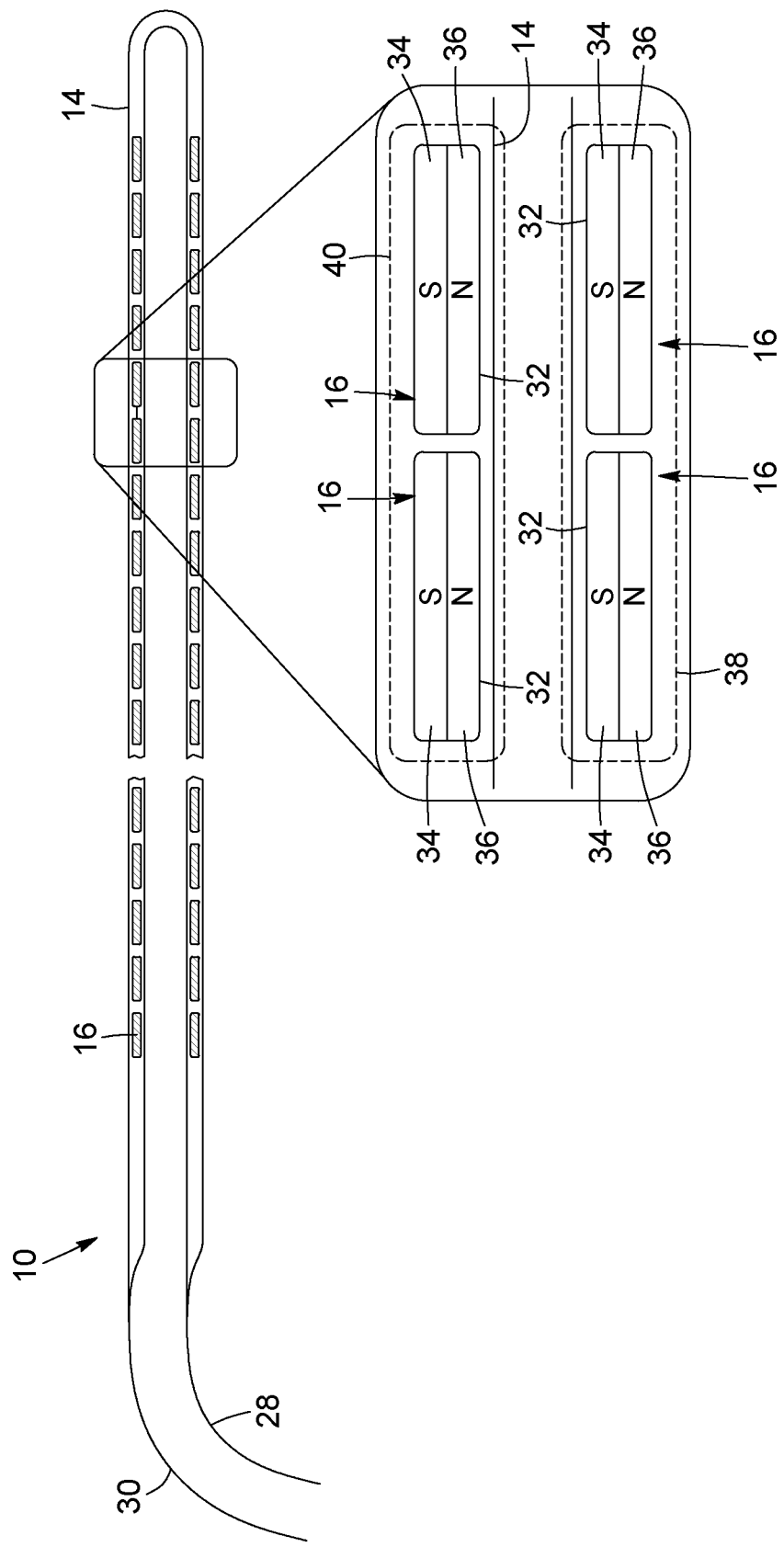
FIG. 5 is a side cross-sectional view schematic of a partitioning device in a looped pre-partitioning configuration, with an enlarged view of magnet elements in a first zone of a magnet assembly and magnet elements in a second zone of the magnet assembly.

With reference now to FIGS. 4 and 5, each one of the magnet elements 16 can be a dipole magnet having magnetic poles across the thickness of the magnet element 16, such that the magnet element 16 includes a first magnetic pole 34 on one side thereof and a second magnetic pole 36 on another side thereof, the second magnetic pole 36 being different than the first magnetic pole 34. One side of the magnet element 16 corresponds to a magnet-coupling side 32, which is the side of the magnet element 16 that will eventually face the tissue 26 of the hollow organ to be treated once the magnet assembly 12 is installed around the outer surface of the target hollow organ, which is also referred to above as the top side 18 of the magnet element 16.

Figure 7:
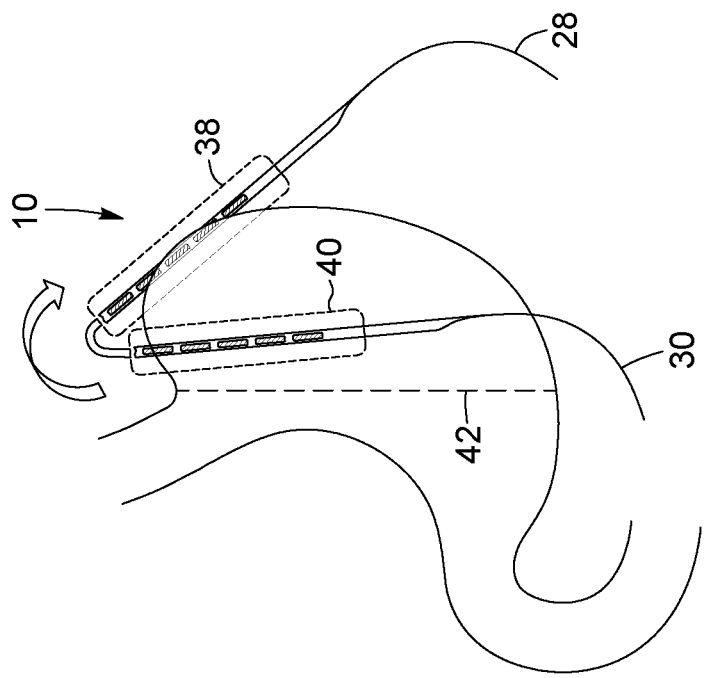
FIG. 7 is a top cross-sectional view schematic of the partitioning device shown in FIG. 6 and being folded around the outer surface of the stomach to be placed in a looped pre-partitioning configuration.
Figure 6:
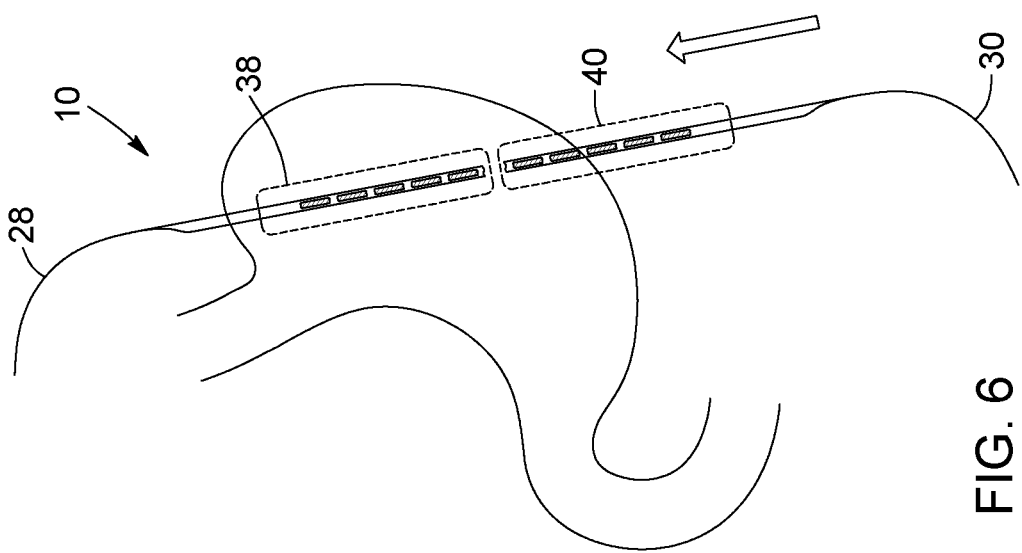
FIG. 6 is a top cross-sectional view schematic of a partitioning device in an extended pre-partitioning configuration shown for subsequent placement around an outer surface of the stomach.

The magnet elements 16 are positioned strategically along the length of the magnet assembly 12 to obtain a desired functionality of the magnet assembly 12. With reference to FIGS. 1-10, a first zone 38 and a second zone 40 of the magnet assembly 12 are represented. The first zone 38 of the magnet assembly 12 corresponds to a portion of the magnet assembly 12 that would be the first to be inserted into the abdominal cavity of the patient, when the partitioning device 10 is in an extended pre-partitioning configuration such as in FIG. 1, by guiding the leading elongated member 28 into the abdominal cavity, such as in FIG. 6. Then, the first zone 38 of the magnet assembly 12 would be the one that is flipped around the outer surface of the target hollow organ in a posterior position, such as shown in FIG. 7. The second zone 40 corresponds to a portion of the magnet assembly 12 that follows the first zone 38 when then magnet assembly 12 is inserted into the abdominal cavity, and then that remains in an anterior position without being flipped around the outer surface of the target hollow organ, such as shown in FIG. 7.

Figure 10:
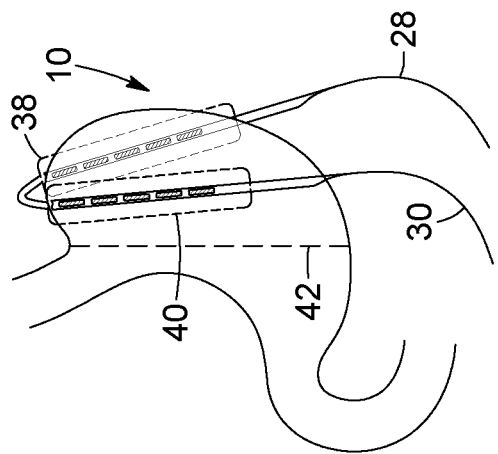
FIG. 10 is a top cross-sectional view schematic of the partitioning device shown in FIG. 9 and placed around the outer surface of the stomach in the looped pre-partitioning configuration.
Figure 9:
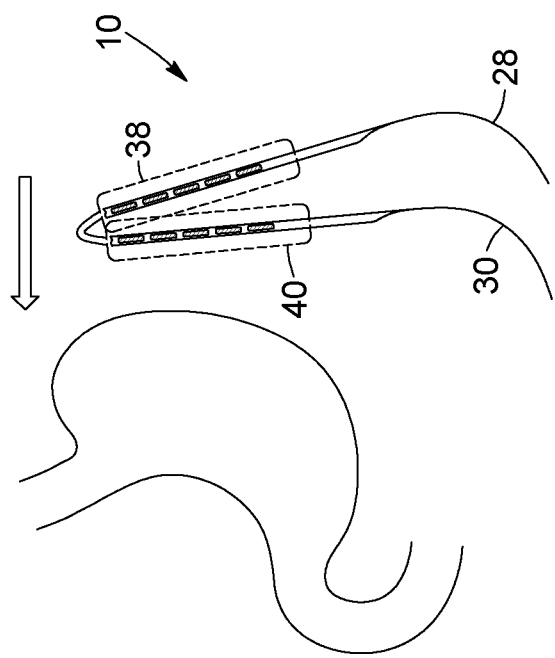
FIG. 9 is a top cross-sectional view schematic of the partitioning device shown in FIG. 8 and being translated for placement around the outer surface of the stomach.
Figure 8:
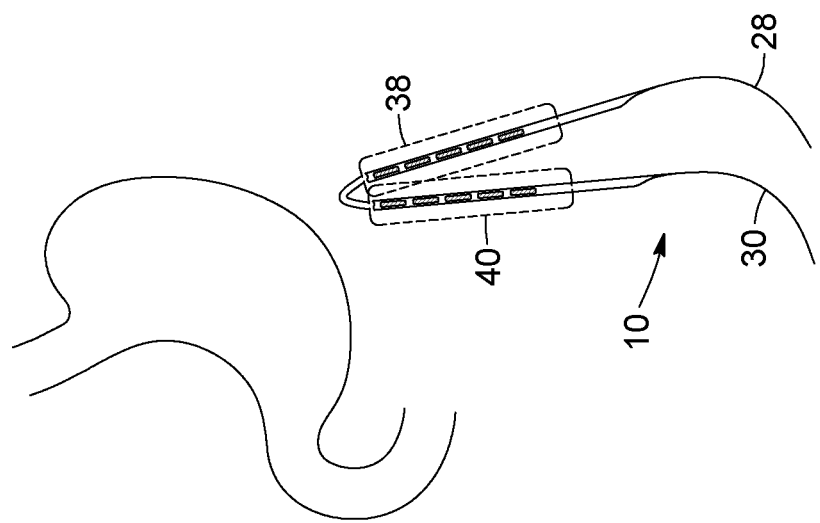
FIG. 8 is a top cross-sectional view schematic of a partitioning device in a looped pre-partitioning configuration shown for subsequent placement around an outer surface of the stomach.

Referring to FIGS. 8-10, in implementations where the magnet assembly 12 is already in a looped pre-partitioning configuration, the first and second zone 38, 40 of the magnet assembly 12 can be navigated in the abdominal cavity side-by-side rather than being extended. In such implementations, the first zone 38 of the magnet assembly 12 can be said to correspond to a portion of the magnet assembly 12 that would be in a posterior location once inserted in the abdominal cavity of the patient, and the second zone 40 can be said to correspond to a portion of the magnet assembly 12 that would be in a posterior location once inserted in the abdominal cavity of the patient, or vice-versa.

Referring back to FIGS. 4 and 5, the first zone 38 includes a series of magnet elements 16 that each has a magnet-coupling side 32 having a same magnetic pole among each other (i.e., a first zone magnetic pole), and the second zone 40 includes a series of magnet elements 16 that also each have a magnet-coupling side 32 having a same magnetic pole among each other (i.e., a second zone magnetic pole), but that is different from the magnetic pole of the magnet-coupling side 32 of the magnet elements 16 of the first zone 38. The magnet-coupling side 32 corresponds to the top side 18 of the magnet element 16 described above, i.e., the side that faces the walls of the hollow organ. For instance, as shown in FIG. 4, the partitioning device 10 is in an extended pre-partitioning configuration, and the second zone 40 of the magnet assembly 12 is longitudinally spaced apart from the first zone 38. The magnet-coupling side 32 of the magnet elements 16 of the first zone 38 has a North pole, and the magnet-coupling side 32 of the magnet elements 16 of the second zone 40 has a South pole. Similarly, in FIG. 5, the partitioning device 10 is in a looped pre-partitioning configuration, and the magnet-coupling side 32 of the magnet elements 16 of the first zone 38 has a North pole, and the magnet-coupling side 32 of the magnet elements 16 of the second zone 40 has a South pole.

This configuration of the magnet assembly 12, with the magnet elements 16 having a different magnet-coupling side 32 depending on the zone 38, 40 that they are in along the magnet assembly 12, enables the magnet elements 16 of the first zone 38 and the second zone 40 of the magnet assembly 12 to attract each other and magnetically couple once the magnet assembly 12 is in the partitioning configuration.

As mentioned above, the magnet elements 16 can have various shapes and sizes. The choice of the shape and/or the size of the magnet elements 16 can depend on the target hollow organ around which the partitioning device 10 will be implanted. For instance, for an organ like the stomach that is substantially larger and flatter than portions of the small intestine such as the duodenum, the jejunum, or the colon, elongated magnet elements 16 can be used as part of the magnet assembly 12. On the other hand, the length of the magnet element 16 can remain sufficiently small to permit the navigation of the magnet assembly 12 around the outer surface of the stomach, or another target hollow organ. For instance, in some implementations, magnet elements 16 designed to partition a biliary duct may have a size ranging from about 2 mm to about 10 mm, whereas magnet elements 16 designed to partition a stomach may have a size ranging from about 2 cm to about 10 cm. As a general relationship between the size of the magnet elements 16 and the target hollow organ, magnet elements 16 designed to partition a hollow organ that is thicker and/or larger can generally be larger than magnet elements 16 designed for a smaller and/or thinner hollow organ. This general relationship takes into consideration the principle that larger and/or thicker hollow organs may beneficiate from a larger attractive force conferred by larger magnet elements 16 to achieve a desired compression of the walls of the hollow organ and subsequent healing of the edges surrounding the magnet elements 16. In some implementations, for a magnet assembly 12 configured in looped pre-partitioning configuration, magnet elements 16 may be longer than for a magnet assembly 12 configured in an extended pre-partitioning configuration, since in the looped pre-partitioning configuration, the magnet assembly 12 is already folded on itself.

In addition, although the magnet elements 16 of a portion of a magnet assembly 12 exemplified in FIGS. 3 and 11-16 are represented as being substantially rectangular, it is to be understood that the magnet elements 16 can include tapered edges, beveled edges, rounded edges, and the like. The magnet elements 16 can also have an oblong shape, stadium shape, a circular shape, a triangular shape, a rectangular shape, an octagonal shape or any other shape suitable for applications described herein.

Figure 17:
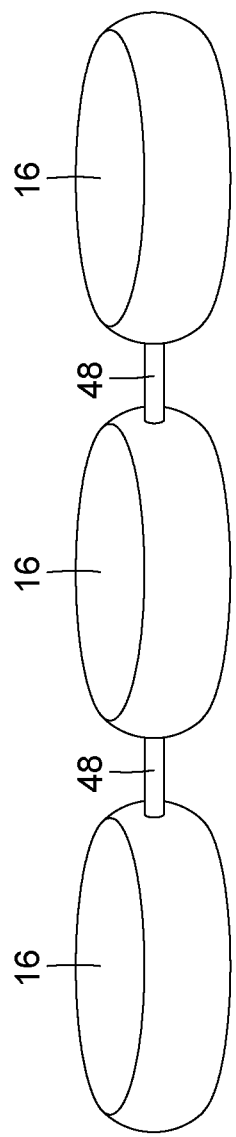
FIG. 17 is a perspective view schematic of three magnet elements of a portion of a magnet assembly shown in an arbitrary spatial relationship, each magnet element having rounded edges, and adjacent magnet elements being flexibly joined together by a flexible connector.

For instance, FIG. 17 illustrates an example of a series of magnet elements 16 of a portion of a magnet assembly 12, each magnet element 16 having rounded edges and a substantially oval shape. In some implementations, magnet elements 16 having rounded edges or other non-sharp features can contribute to facilitate movement between adjacent magnet elements 16 and thus provide an enhanced flexibility to the magnet assembly 12.

Figure 18:
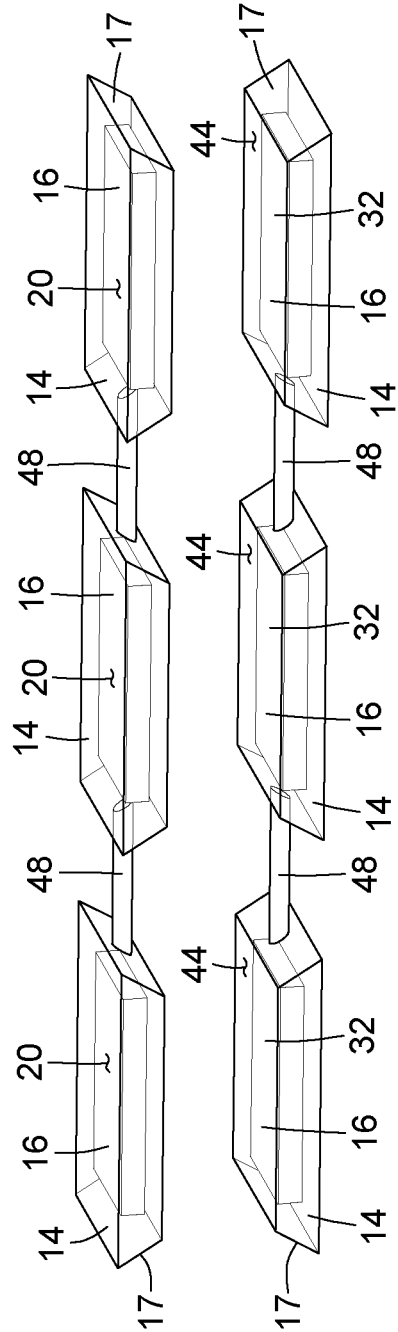
FIG. 18 is a perspective view schematic of six magnet elements of a portion of a magnet assembly shown in an arbitrary spatial relationship, each magnet element being received in a corresponding housing, the housing having bevelled edges, adjacent magnet elements being flexibly joined together by a flexible connector extending between corresponding housings, and the magnet elements being shown facing each other.

FIG. 18 illustrates an example of a series of magnet elements 16 of a portion of a magnet assembly 12, each magnet element 16 being received in a housing having beveled edges 17, the magnet elements 16 being shown facing each other as would be the case when placed on either side of the walls of the target hollow organ.

Figure 19:
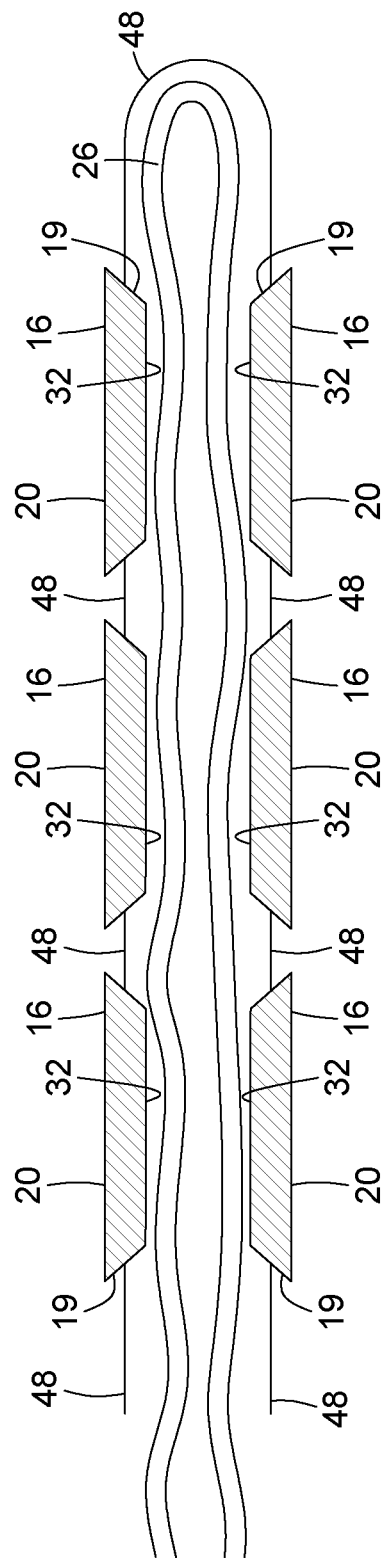
FIG. 19 is a side cross-sectional view schematic of six magnet elements of a portion of a magnet assembly shown in an arbitrary spatial relationship, each magnet element having bevelled edges, adjacent magnet elements being flexibly joined together by a flexible connector, the magnets being shown with walls of a hollow organ therebetween.

FIG. 19 illustrates an example of magnet elements 16 of a portion of a magnet assembly 12, each magnet element 16 having beveled edges 19. In some implementations and as illustrated in FIG. 18 or 19, when magnet elements 16 or a housing 14 include beveled edges, the magnet-coupling side 32 of the magnet element 16 or the organ-contacting side 44 of the housing 14 can have a smaller surface area compared to the side located further away from the walls of the hollow organ, i.e., the bottom side 20. This configuration can allow for a smaller compression surface between magnet-coupling sides 32 of opposite magnet elements 16 or between organ-contacting sides 44 of opposite housings 14, such that if the ischemic necrosis was to occur more rapidly than initially foreseen, the side of the magnet elements 16 or housings 14 having a larger surface area can provide an anchor to prevent undesired movements of the magnet elements 16 or housing 14. In some implementations, the side of the magnet elements 16 or housing 14 having a larger surface area can also contribute to prevent the magnet elements 16 or housing 14 to pass through an area of the walls of the hollow organ where ischemic necrosis has occurred.

In some implementations, the magnet-engaging side 32 of the magnet elements 16 included in the first zone 38 of the magnet assembly 12 can have a complimentary shape with regard to the magnet-engaging side 32 of the magnet elements 16 included in the second zone 40 of the magnet assembly 12. For instance, the magnet-engaging side 32 of the magnet elements 16 included in the first zone 38 can include a recess, and the magnet-engaging side 32 of the magnet elements 16 included in the second zone 40 can include a projection configured to fit within the recess. In some implementations, the engagement of the recess with a corresponding projection, or of other features having complimentary shape, can contribute to stabilize the magnet elements 16 of the first zone 38 with those of the second zone 40. In some implementations, the edges of the magnet elements 16 included in the first zone 38 of the magnet assembly 12 can include a rabbeted edge, and the edges of the magnet elements 16 included in the second zone 40 of the magnet assembly 12 can include a rabbeted edge that is complimentary to the one of the magnet elements 16 of the first zone 38.

In some implementations and as mentioned above, the attractive force of the magnet elements 16 can be chosen according to the thickness and/or to the composition of the target hollow organ along the partition line 42. For instance, the attractive force of the magnet elements 16 can be proportional to the thickness of the target hollow organ wall. This principle can apply from one target hollow organ to another, or within the same target hollow organ. For example, the wall of the stomach being thicker than the wall of the duodenum or of another portion of the small intestine, the attractive force of the magnet elements 16 for a magnet assembly 12 designed for the stomach may be higher than for a magnet assembly 12 designed for the duodenum.

When the wall thickness varies within the same target hollow organ, the attractive force of the magnet elements 16 can vary within the first zone 38 and accordingly within the second zone 40 such that the pressure exerted on the tissue of the target hollow organ along the length of the magnet assembly 12 once in the partitioning configuration can also vary. For instance, when the target hollow organ is the stomach, the wall thickness of the stomach is larger near the fundus compared to the wall thickness in the body or the antrum of the stomach. Accordingly, the magnet elements 16 of the magnet assembly 12 can be chosen to have a higher attractive force in an upper portion of the magnet assembly 12, i.e., closer to the transition from the first zone 38 to the second zone 40, compared to the attractive force of the magnet elements 16 of the magnet assembly 12 in a lower portion of the magnet assembly 12, i.e., away from the transition for the first zone 38 to the second zone 40. In the context of the example related to the stomach, the relative terms "upper" and "lower" are used to refer to portions of the magnet assembly 12 once implanted around the outer surface of the stomach and when the patient is standing up, with the "upper" portion corresponding to a portion of the stomach in the area of the fundus, and the "lower" portion corresponding to a portion of the stomach in the area of the body or the antrum.

In implementations where the target hollow organ is mainly composed of muscular fibers, such as the distal colon or the rectum, the attractive force of the magnet elements 16 may be chosen to be higher than the attractive force of the magnet elements 16 for a magnet assembly 12 designed for portions of the small intestine such as the duodenum, the jejunum or the ileum.

The attractive force of the magnet elements 16 can also be chosen so as to facilitate placement and implantation of the partitioning device 10 around the target hollow organ. For instance, in some implementations, the attractive force between the magnet elements 16 can be sufficiently weak to enable magnetic uncoupling of the magnet elements 16 during the placement of the partitioning device 10 along the partition line 42, such that trial and error may be possible to arrive at the desired location of the magnet assembly 12.

Furthermore, the attractive force of the magnet elements 16 can also be chosen in function of the planned healing period. For example, the attractive force between the magnet elements 16 can be sufficiently weak to favor a healing period in a range of days or weeks. A longer healing period can facilitate the obtention of well-fused walls and a progressive application of pressure along the partitioning line, whereas magnet elements 16 that would have a too strong attractive force could cause rapid ischemic pressure necrosis between the magnet-coupling sides 32 of the magnet elements 16, which could impair the healing mechanism on the edges of the magnet elements 16 and could result in an opening in the tissue of the target hollow organ. In some implementations, the attractive force of the magnet elements 16 can be chosen such that the healing process occurs over a period of between 2 to 7 weeks following implantation of the partitioning device 10. In some implementations, the attractive force of the magnet elements 16 is chosen such that the healing process occurs over a period of between 3 to 6 weeks following implantation of the partitioning device 10. Other durations of healing periods are also possible depending on the desired result and the target hollow organ.

It is to be noted that in some implementations, the ischemic pressure necrosis to which is subjected the walls of the target hollow organ along the partition line 42 may be sufficient to lead to a partition of the target hollow organ along the partition line 42 with the fused tissue on the edges of the magnet elements 16. In other implementations, the ischemic pressure necrosis to which is subjected the walls of the target hollow organ along the partition line 42 may be sufficient to lead to a separation of the partitioned section of the target hollow organ. The attractive force of the magnet elements 16 can thus also be chosen according to whether a partition of the target hollow organ or a separation of a portion of the target hollow organ is desired.

Monitoring the healing process through time also plays a role in the result obtained on the target hollow organ following the implantation of the partitioning device 10, and such monitoring can be helpful in determining at which moment to proceed with the removal of the partitioning device 10 to obtain the desired result with regard to partitioning of the target hollow organ or separation of a portion of the target hollow organ.

In some implementations, the size of the magnet elements 16 can vary along the length of the magnet assembly 12. This variation in the size of the magnet can contribute to increase the flexibility of the magnet assembly 12 in selected portions thereof, in particular when the magnet assembly 12 includes multiple magnet elements 16 individually received in a housing 14 or without a housing, such as shown in FIGS. 12-15 and 18. For instance, the magnet assembly 12 can include smaller magnet elements 16 in proximity of the transition from the first zone 38 to the second zone 40. Smaller magnet elements 16 provided in proximity of this transition zone can contribute to facilitate the adoption of the looped pre-partitioning configuration and the partitioning configuration, by facilitating the folding over of the magnet assembly 12 such as shown in FIG. 7. Smaller magnet elements 16 in proximity of the transition from the first zone 38 to the second zone 40 can thus facilitate the placement of the partitioning device 10. In some implementations, larger magnet implants, especially in terms of length, away from this transition zone can facilitate the obtention of a continuous partition line 42.

Housing

With reference to FIGS. 11-16 and 18, in some implementations, the magnet elements 16 can be received in a housing 14. In FIG. 11, a single magnet element 16 is received in a corresponding housing 14, while in FIG. 12, multiple magnet elements 16 are received in a single housing 14. In other implementations, a certain number of magnet elements 16 can be received in a housing 16. For instance, 2 to 10 magnet elements 16 can be received in a single housing 14. In such implementations, the number of magnet elements 16 in the housing 14 can be influenced by their size, i.e., the smaller the magnet elements 16, the more successive magnet elements 16 can be received in a housing 14 having a given length.

Figure 13:
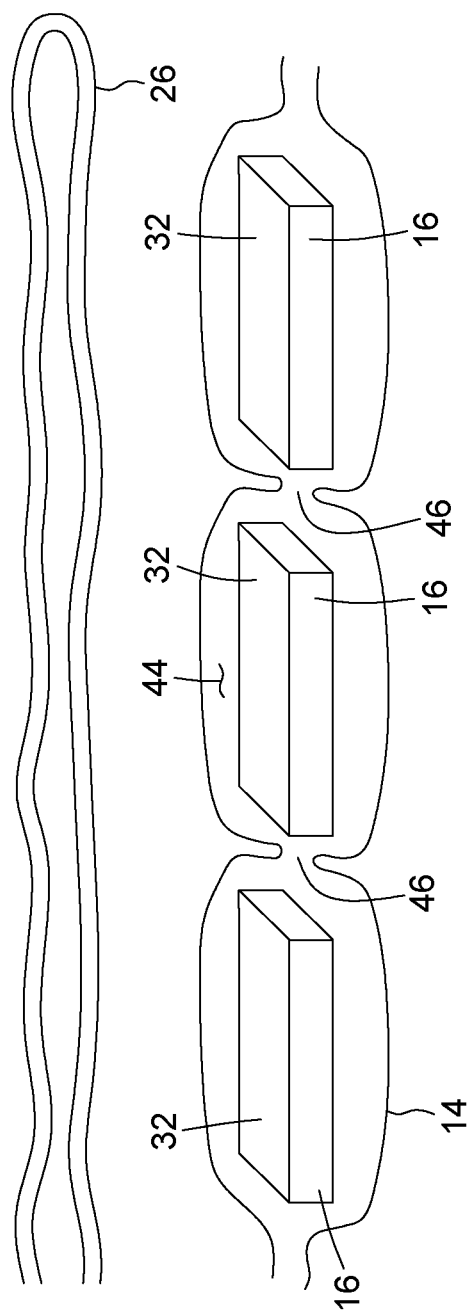
FIG. 13 is a perspective view schematic of three magnet elements of a portion of a magnet assembly shown in an arbitrary spatial relationship relative to walls of a portion of a hollow organ, the magnet elements being received in a corresponding housing having rounded edges, the successive housings being flexibly joined together by a thinner extension of the housing.

As mentioned above, the housing 14 includes an organ-contacting side 44 that is in contact with the tissue of the target hollow organ when the partitioning device 10 is in the partitioning configuration. In some implementations, the organ-contacting side 44 of the housing 14 includes an elongated flat contact surface to facilitate an even contact with the tissue compressed therebetween. The housing 14 can be configured to provide an atraumatic surface which can contribute to avoid damage to surrounding tissues. The housing 14 can include rounded edges, and/or tapered transitions between its walls. In some implementations, the housing 14 can have an oblong shape or a stadium shape. FIG. 13 illustrates an example of magnet elements 16 received in a respective housing 14 having rounded edges, the successive housings 14 being flexibly joined together by a thinner extension 46 of the housing 14, also referred to as a connecting portion of the housing 14. Additional details are provided below regarding this aspect.

In some implementations, the organ-contacting side 44 of the housing 14 of the magnet elements 16 included in the first zone 38 can include a recess, and the organ-contacting side 44 of the housing 14 of the magnet elements 16 included in the second zone 40 can include a projection configured to fit within the recess. The engagement of the recess with a corresponding projection, or of other features having complimentary shape, via the housings 14 can contribute to stabilize the magnet elements 16 of the first zone 38 with those of the second zone 40. In some implementations, the edges of the organ-contacting side 44 of the housing 14 of the magnet elements 16 included in the first zone 38 of the magnet assembly 12 can include a rabbeted edge, and the edges of the organ-contacting side 44 of the housing 14 of the magnet elements 16 included in the second zone 40 of the magnet assembly 12 can include a rabbeted edge that is complimentary to the one of the housings 14 of the first zone 38.

In some implementations, the housing 14 can contribute to spreading the force applied by the magnet element(s) 16 over a larger area, which can be advantageous depending on the application and/or on the target hollow organ. The housing 14 can be made of a biocompatible material. In some implementations, the housing 14 can be made of a metal such as stainless steel, titanium, or other medical implant grade metals. Alternatively, the housing 14 may be made of silicone, or other medical implant grade polymers. In certain scenarios, the housing 14 is made of Silastic™, which is a flexible silicone elastomer. In some implementations, the housing 14 can provide a protective coating around the magnet element(s) 16, which in turn can help preventing corrosion and maintaining the integrity of the magnet element 16. The texture of the housing 14, in particular on the organ-contacting side 44, can be chosen to provide an increased stability to the magnet assembly 12 once in the partitioning configuration. For instance, the surface roughness of the implant on the organ-contacting side 44 of the housing 14 can be higher than on the opposite side thereof. The surface roughness of the organ-contacting side 44 of the housing 14 may be beneficial once the magnet elements 16 are magnetically coupled to prevent magnetic decoupling due to shear forces.

Flexible Connection Between Adjacent Magnet Elements

As mentioned above, the magnet assembly 12 includes magnet elements 16 that are flexibly connected to each other in series. Flexibly connecting the magnet elements 16 together can be achieved in various ways. Examples are provided below.

With reference to FIG. 13, multiple magnet elements 16 can be received in a respective single housing 14, and the housing 14 can include portions in between adjacent magnet elements 16 that are adapted to provide an increased flexibility to the magnet assembly 12. As shown in FIG. 13, these portions 46 can be narrower, or thinner, to increase their freedom of movement, while remaining sufficiently robust to avoid breaking. In some implementations, the portion 46 of the housing 14 between adjacent magnet elements 16 can be made of a material that is different from the material of the rest of the housing 14, to benefit from specific characteristics of this different material, in particular in terms of its flexibly. In some implementations, the portion 46 of the housing 14 between adjacent magnet elements 16 can offer a certain range of motion in a certain plan, while offering a restricted range of motion in another plan. For example, it may be desired to have the magnet elements 16 move relative to each other to enable the magnet assembly 12 to fold around the target hollow organ, while it may be less desirable to have the magnet elements 16 move laterally relative to each other, as lateral movement of the magnet elements 16 could contribute to veering the magnet elements 16 off the partition line 42.

Figure 14:
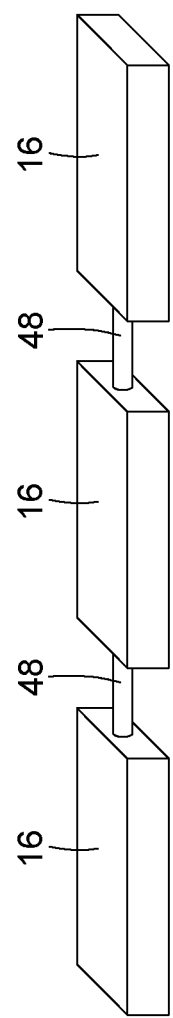
FIG. 14 is a perspective view schematic of three magnet elements of a portion of a magnet assembly shown in an arbitrary spatial relationship, adjacent magnet elements being flexibly joined together by a flexible connector.

With reference to FIG. 14, when no housing is provided around the magnet elements 16, the magnet elements 16 can include a hook (not shown) on each lateral side thereof, and be connected to each other via a flexible connector 48, such as a string. The type of flexible connector 48 can be chosen to provide sufficient mobility and flexibility to the magnet assembly 12 according to a given range of movement, so that the magnet assembly 12 can easily be guided to its destination in the abdominal cavity and placed around the target hollow organ. For example, when the target hollow organ is substantially cylindrical such as the duodenum or the colon, the circumference of such organs can be relatively small compared to the size of the stomach, and it may be beneficial to have a magnet assembly 12 having an increased flexibility to facilitate guiding the partitioning device 10 around the organ and maintaining it in place.

Figure 15:
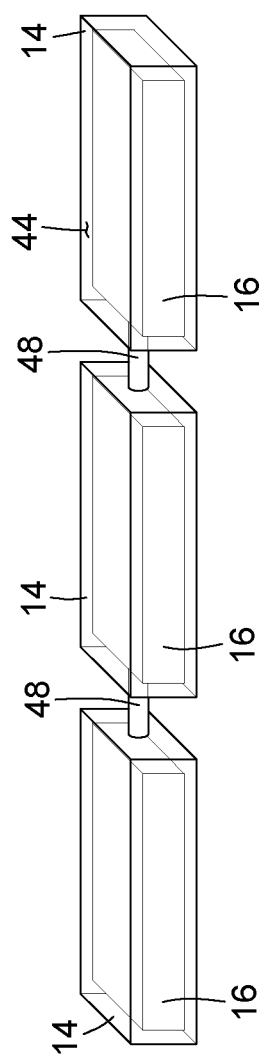
FIG. 15 is a perspective view schematic of three magnet elements of a portion of a magnet assembly shown in an arbitrary spatial relationship, each magnet element being received in a corresponding housing, and adjacent magnet elements being flexibly joined together by a flexible connector extending between corresponding housings.

With reference to FIG. 15, a flexible connector 48 can be provided between adjacent magnet elements 16 that are individually housed in a respective housing 14. In such implementations, an engaging portion, such as a hook, can be provided on the lateral sides of the housing 14. In some implementations, the engaging portion can be integral with the housing 14. The housing 14 can thus be molded as a single piece unit that includes a hook on each lateral side thereof, with the magnet element 16 received in the housing 14, and adjacent ones of the multiple magnet elements 16 can be flexibly connected to each other via a flexible connector 48 engaged with respective hooks. Alternatively, a hook can be provided on a lateral side of the housing 14, and a flexible connector 48 can extend from another side to flexibly connect with a hook of an adjacent housing 14.

Figure 16:
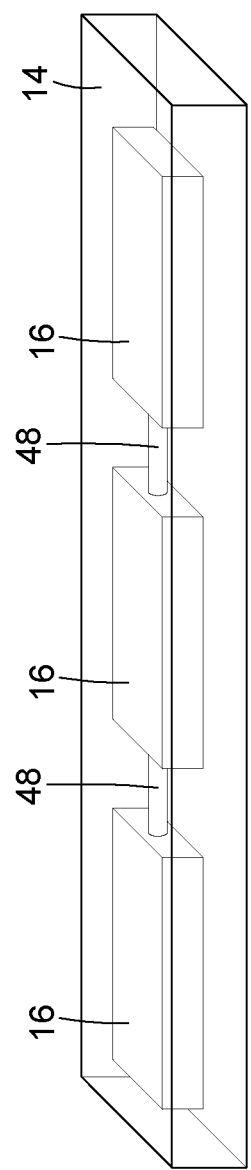
FIG. 16 is a perspective view schematic of three magnet elements of a portion of a magnet assembly shown in an arbitrary spatial relationship, the magnet elements being received in a corresponding housing, and the magnet elements being flexibly joined together within the housing by a flexible connector extending between adjacent magnet elements.

In other implementations and with reference to FIG. 16, the magnet elements 16 can be flexibly connected to each other by being integrated within the housing 14, and a flexible connector 48 can also be provided between adjacent magnet elements 16 within the housing 14. In the implementation shown in FIG. 16, in contrast to the implementation shown in FIG. 15, the flexible connectors 48 are thus shown integrated within the housing 14.

It is to be understood and as shown in FIG. 12, that the flexibility of the magnet assembly 12 can be provided by the presence of the housing 14 itself around the magnets elements 16, for instance given the flexibility of the material from which is made the housing 14.

The distance between adjacent magnet elements 16 can be chosen so as to have an impact on the resulting flexibility of the magnet assembly 12. In some implementations, when determining the distance between adjacent magnet elements 16, care should be taken to maintain an equilibrium between the flexibility of the magnet assembly 12 obtained in such manner and the impact on the resulting partition line 42, as successive magnet elements 16 that may be too distant apart from each other may result in a less uniform partition line 42. In some implementations, the distance between adjacent magnet elements 16 can vary along the length of the magnet assembly 12, similarly to what is described above regarding the size of the magnet elements 16. For instance, in some implementations, magnet elements 16 located in proximity of the transition from the first zone 38 to the second zone 40 may be provided slightly further apart to provide enhanced flexibility to the magnet assembly 12 in this transitioning area. In some implementations, the interplay between the size of the magnet elements 16 and the distance between adjacent magnet elements 16 can contribute to provide an enhanced flexibility to the magnet assembly 12 and a desired partition line 42. In some implementations, magnet elements 16 provided as close as possible to each other can be favored as long as flexibility of the magnet assembly 12 is preserved. In that respect and as mentioned above, magnet elements 16 or housings 14 having rounded edges can be advantageous to provide magnet elements 16 or housings 14 close together but without compromising flexibility of the magnet assembly 12. It is to be noted that these are examples only to illustrate the effect that the various configurations may have on the flexibility of the magnet assembly 12, and that multiple configurations of the magnet assembly 12 can be implemented to achieve a combination of a desired flexibility of the magnet assembly 12 and a desired partition line 42 and corresponding healing of the tissue on the edges of the magnets elements 16.

Positioning and Implantation of the Partitioning Device

With reference now to FIGS. 20-29, implementations related to the implantation of the partitioning assembly at various locations for a given target hollow organ, and for different target hollow organs, will be now described.

FIG. 20 illustrates an example of a partitioning device 10 in a partitioning configuration, with opposite walls of the target hollow organ being compressed between the organ-contacting sides 44 of the housing 14, and the magnet-engaging sides 32 of the magnet elements 16 from the first zone 38 being magnetically coupled to the magnet-engaging sides 32 of the magnet elements 16 from the second zone 40. The partitioning device 10 can be implanted along a desired partition line 42, and examples of locations of the partition line 42 are provided below.

FIG. 21 illustrates an example of a partitioning device 10 in a partitioning configuration, showing a top view of the partitioning device 10. The partitioning device 10 shown in FIG. 21 includes a curved region 21. The curved region 21 can be provided for instance by the shape of the housing 14, or by the way the magnet elements 16 are joined together. In some implementations, curved magnet elements 16 can also be provided. The shape and location of the curved region 21 can vary, and FIG. 21 is only an example shown for illustrative purposes. This type of configuration of the partitioning device 10, i.e., a partitioning device 12 that includes a curved region 21, can be advantageous for placement of the partitioning device 12 around a tumor or around a portion of a transverse colon, for instance.

Figure 22:
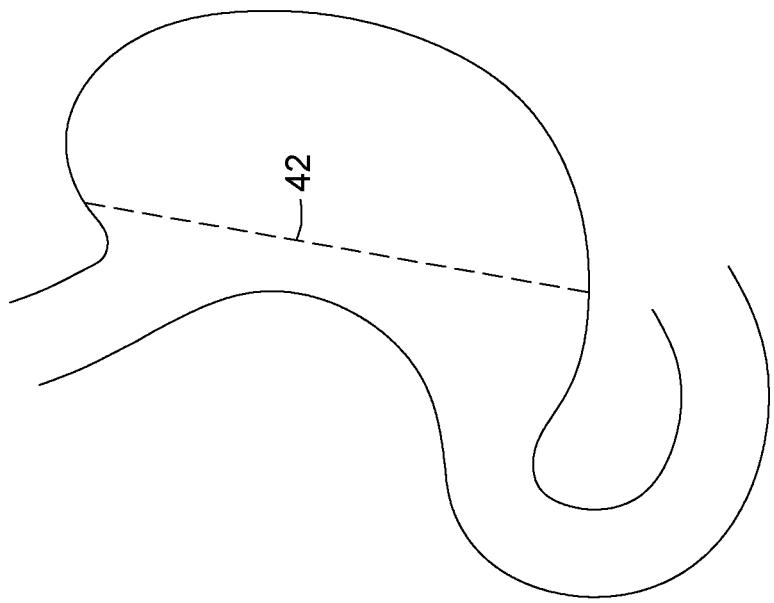
FIG. 22 is a front view schematic of a stomach, showing a complete vertical partition line between the lesser curvature and the greater curvature of the stomach.

FIG. 22 illustrates an example of a complete vertical partition line 42 that extends from the fundus to the antrum and between the lesser curvature and the greater curvature of the stomach, to obtain a vertical sleeve configuration of the stomach following healing of the tissue on the edges of the magnet elements 16. The location of the partition line 42 can vary depending on the volume of the areas of the stomach that are desired to be obtained. In such implementations, the magnet assembly 12 can be placed at a desired location around the outer surface of the stomach by inserting the partitioning device 10 in an extended pre-partitioning configuration in the abdominal cavity and placing it around the outer surface of the stomach as shown in FIG. 7. The insertion and guiding of the magnet assembly 12 can be done laparoscopically for a minimally invasive procedure, which also advantageously enables minimal disturbance of the connective tissue, arteries, veins and other organs surrounding the stomach. When inserting the magnet assembly 12 into the abdominal cavity in the extended pre-partitioning configuration, the magnet assembly 12 can be navigated around the outer surface of the stomach, and aligned with the desired partition line 42. Once a proper alignment of the magnet assembly 12 is obtained, the magnet elements 16 of the first zone 38 of the magnet assembly 12 can be brought in sufficiently close proximity of the magnet elements 16 of the second zone 40 of the magnet assembly 12 such that the magnet-engaging sides of the magnet elements 16 of the first zone 38 can be magnetically coupled to the magnet-engaging sides of the magnet elements 16 of the second zone 40. As mentioned above, the attractive force of the magnet elements 16 can be chosen to enable trial and error until proper placement of the magnet assembly 12 is achieved.

Alternatively, placement of the magnet assembly 12 can be performed during an open surgery. In such cases, the magnet assembly 12 can be provided for placement around the stomach either in the extended pre-partitioning configuration or in the looped pre-partitioning configuration. Multiple other techniques can also be used to position and implant the magnet assembly 12. For instance, image-guided procedures (e.g., ultrasound, magnetic resonance imaging, computed tomography and the like) and flexible endoscopy are techniques that can be used to insert and/or position the magnet assembly 12 adequately around the target hollow organ. It is to be noted that any other suitable techniques allowing to insert and/or place the magnet assembly 12 around the outer surface of the target hollow organ can also be used.

Figure 23:
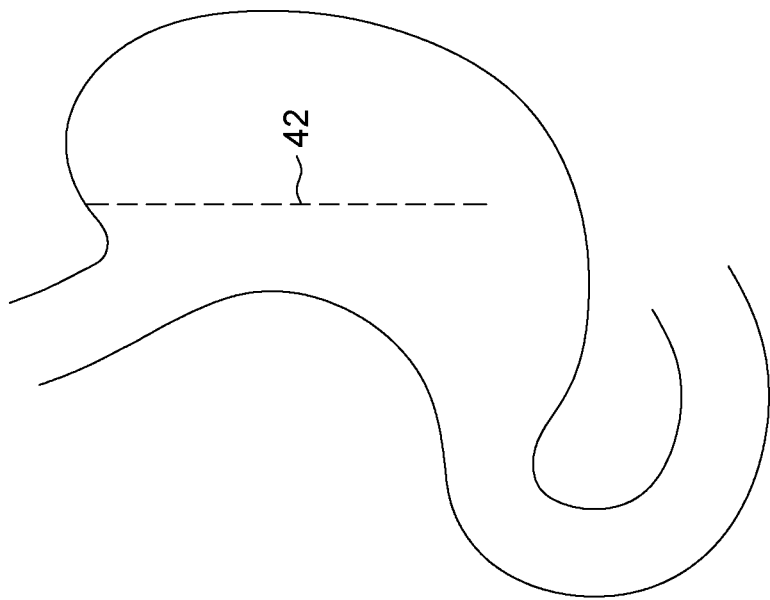
FIG. 23 is a front view schematic of a stomach, showing a partial upper vertical partition line between the lesser curvature and the greater curvature of the stomach.
Figure 24:
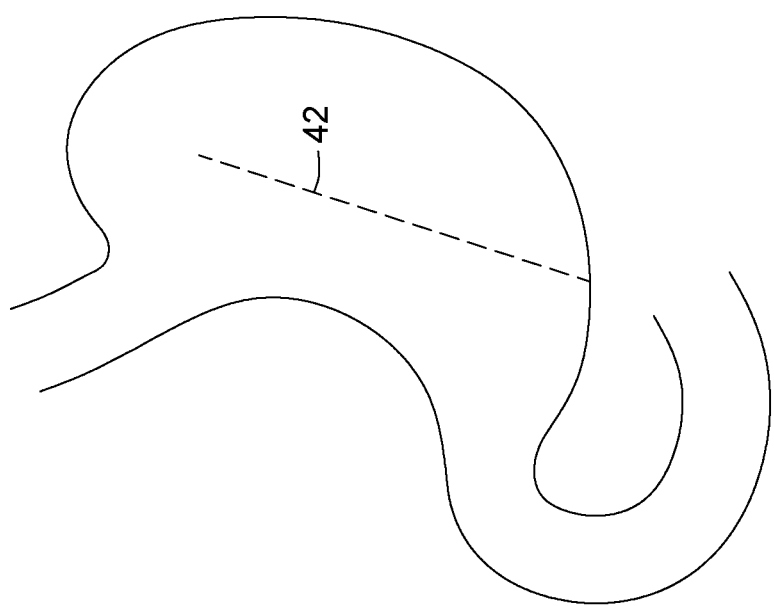
FIG. 24 is a front view schematic a stomach, showing a partial lower vertical partition line between the lesser curvature and the greater curvature of the stomach.

Referring to FIGS. 23 and 24, in some implementations, the partition line 42 can extend substantially vertically along a given portion of the stomach, i.e., without going across the full height of the stomach. In the implementation shown in FIG. 23, the partition line 42 can be referred to as an upper vertical partition line, while in the implementation shown in FIG. 24, the partition line 42 can be referred to as a lower vertical partition line. Similar techniques as those described above for the full height partition line 42 shown in FIG. 18 can be implemented for placement of the magnet assembly 12 around the outer surface of the stomach.

Figure 25:
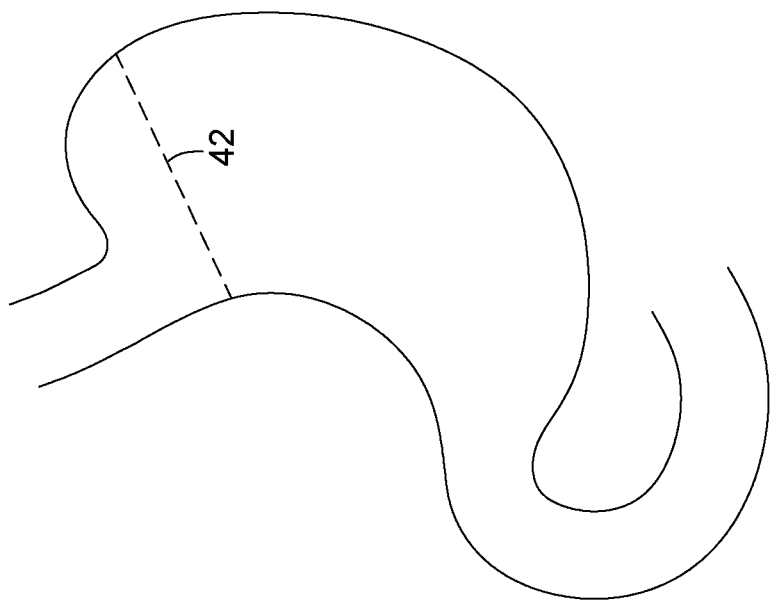
FIG. 25 is a front view schematic of a stomach, showing a complete upper transverse partition line in an upper region thereof.
Figure 26:
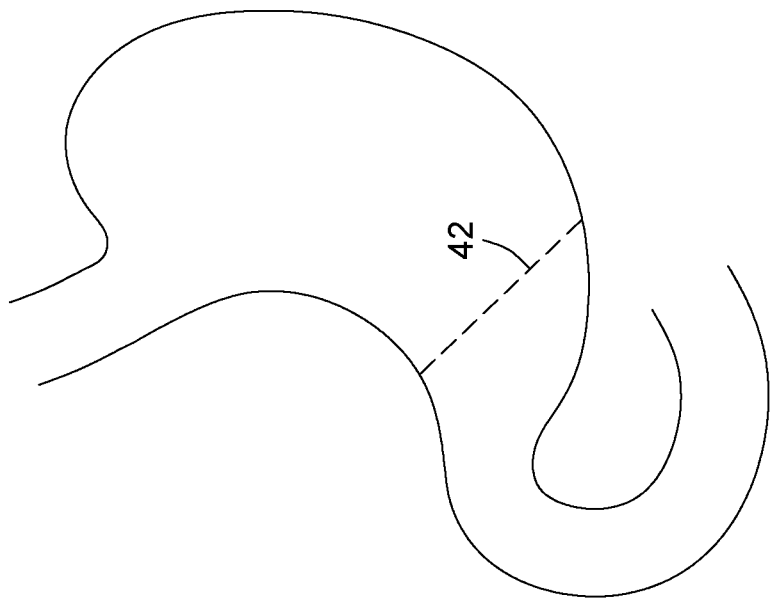
FIG. 26 is a front view schematic of a stomach, showing a complete lower transverse partition line in a lower region thereof.

With reference to FIGS. 25 and 26, in some implementations, the partition line 42 can extend substantially transversally along an upper portion of the stomach (FIG. 25), or along a lower portion of the stomach (FIG. 26), thus providing a complete transverse partitioning of the stomach. A complete transverse partitioning can lead to the formation of a gastric pouch that can be joined to another part of the digestive tract. This type of partitioning can be used in combination with the formation of an anastomosis with a different device to maintain gastrointestinal continuity, where another part of the digestive tract is joined to the partitioned portion of the stomach. For instance, a complete upper partition line 42 can be used to form a Roux-en-Y gastric bypass, such as a retrocolic Roux-en-Y gastric bypass, antecolic Roux-en-Y gastric bypass, and a long limb Roux-en-Y gastric bypass, a mini gastric bypass, a single anastomosis gastric bypass, a duodenal switch, a single anastomosis switch, and other bypasses. In implementations such as shown in FIGS. 25 and 26, a magnet assembly 12 in an extended pre-partitioning can be indicated for a complete transverse placement of the magnet assembly 12 around the outer surface of the stomach, because of the continuous nature of the digestive tract.

Figure 27:
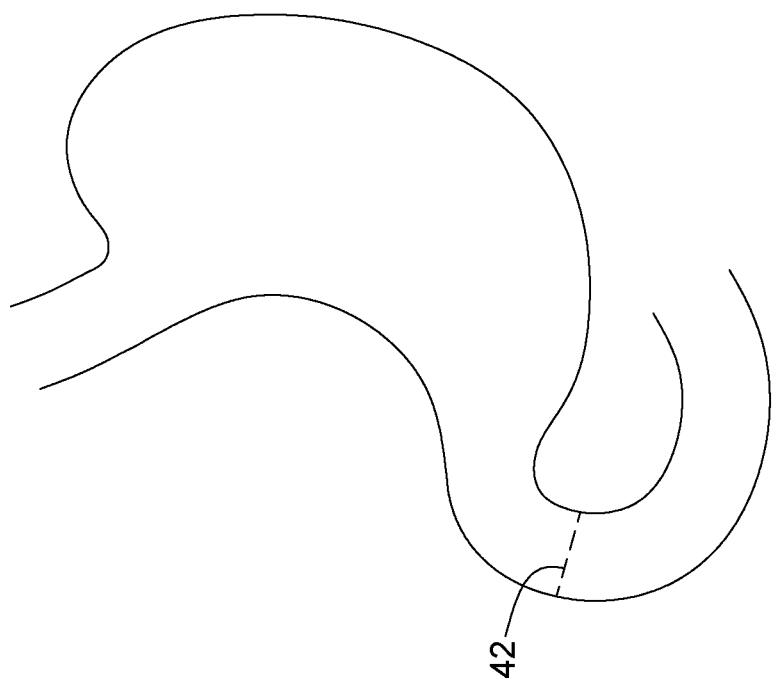
FIG. 27 is a front view schematic of a stomach and a portion of a duodenum, showing a partition line across the duodenum.

FIG. 27 illustrates an implementation of a partition line 42 located in proximity of the pyloric sphincter, around the outer surface of a portion of the digestive tract located in the area of the proximal duodenum. In other implementations, the partition line 42 can be located around the outer surface of a portion of the digestive tract located in the area of the distal duodenum. In yet other implementations, the partition line 42 can be located across any intestinal loop along the duodenum. In yet other implementations, the partition line 42 can be located across any other portion of the small intestine, such as the jejunum or the ileum. Similarly to what is described above with regard to FIGS. 25 and 26, a magnet assembly 12 in an extended pre-partitioning is indicated for placement around the outer surface of the duodenum, again because of the continuous nature of the digestive tract.

Figure 29:
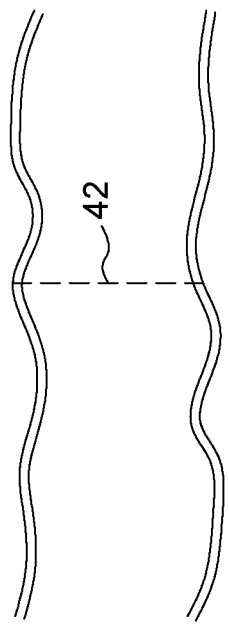
FIG. 29 is a transparent side cross-sectional view schematic of a portion of a proximal colon, showing a complete partition line.
Figure 28:
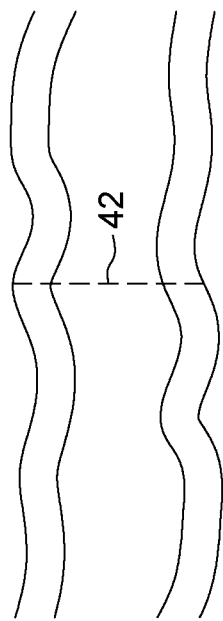
FIG. 28 is a transparent side cross-sectional view schematic of a portion of a distal colon, showing a complete partition line.

FIG. 28 illustrates an implementation of a partition line 42 extending transversally across a portion of a distal colon, where the wall thickness is larger than the wall thickness illustrated in FIG. 29, which shows an implementation of a partition line 42 extending transversally across a portion of a proximal colon.

Method for Implanting the Partitioning Device

A method for partitioning a hollow organ of a digestive tract of a patient using a partitioning device as described herein will now be described in further detail.

The partitioning device includes a leading elongated member and a trailing elongated member, with a magnet assembly extending therebetween. The magnet assembly includes a plurality of magnet elements flexibly connected in series. The leading elongated member can include any type of flexible member. In some implementations, the leading elongated member can be configured for engagement with a delivery catheter to allow the elongated member to be navigated laparoscopically. In some implementations, the trailing elongated member can also include any type of flexible member that can optionally be configured to be engaged with a delivery catheter or to remain outside the patient or in a subcutaneous location. Alternatively, at least one of the leading elongated member and the trailing elongated member can be omitted.

When the leading elongated member is present, the method can include inserting the leading elongated member and the magnet assembly of the partitioning device into an abdominal cavity of the patient. As the partitioning device is an implant that is configured to remain in the abdominal cavity of the patient for a certain period of time, the partitioning device may be sterilized prior to insertion into the abdominal cavity of the patient. For insertion into the abdominal cavity of the patient, the magnet assembly can be either in an extended pre-partitioning configuration or in a looped pre-partitioning configuration. The magnet assembly is then guided to a target hollow organ via the leading elongated member, when present, of the partitioning device, to position the magnet assembly extraluminally around at least a portion of an outer surface of the hollow organ such that an anterior portion of the magnet assembly and a posterior portion of the magnet assembly face each other. Various techniques can be used to insert the magnet assembly into the abdominal cavity of the patient and place the magnet assembly around the outer surface of the target hollow organ. These techniques can include laparoscopic surgery, open surgery, image-guided procedures and flexible endoscopy, for instance. When the anterior portion of the magnet assembly faces the posterior portion of the magnet assembly, the magnet-engaging sides of the magnet elements from a first zone of the magnet assembly face the magnet-engaging sides of the magnet elements from a second zone of the magnet assembly while the magnet elements remain magnetically uncoupled in a looped pre-partitioning configuration to facilitate placement of the magnet assembly along a desired partition line.

Once the magnet elements on both sides of the magnet assembly are aligned as desired along the partition line, the magnet elements can be brought closer together in a partitioning configuration. In the partitioning configuration, the magnet elements of the first zone magnetically couple magnet elements of the second zone, i.e., magnets elements that are facing each other magnetically couple, via their respective magnet engaging sides to compress opposite walls of the hollow organ therebetween. In some implementations, when the magnet elements are received in a housing, the housing includes an organ-contacting side and the opposite walls of the target hollow organ are compressed between the organ-contacting sides of the housing that are facing each other. In some implementations, the organ-contacting side of the housing can be an elongated flat contact surface.

In some implementations, the leading elongated member can be brought in proximity of the trailing elongated member, and one or both of the leading elongated member and the trailing elongated member can be placed outside of the patient or can remain in a sous-cutaneous location. In other implementations, the leading elongated member and the trailing elongated member can be a continuous elongated member that is slidably engaged with the magnet assembly and once the magnet assembly is implanted in the partitioning configuration, the leading elongated member and the trailing elongated member can be removed from the abdominal cavity of the patient by pulling on one of the leading elongated member and the trailing elongated member.

Then, following the implantation of the magnet assembly around the target hollow organ in the partitioning configuration, the magnet assembly is left implanted for a duration of a healing period of time that is sufficient to allow the opposite walls of the hollow organ to fuse together while the magnet elements are magnetically coupled together. In some implementations, the healing period can extend from between 2 weeks to 7 weeks. In some implementations, monitoring the healing process can be performed to determine at which moment the walls of the target hollow organ are well fused together, i.e., with no leaks between the two partitioned portions. The duration of the healing period can depend for instance of the target hollow organ, the configuration of the magnet assembly, the condition of the patient, and various other factors.

Once the walls of the target hollow organ are well fused together and that healing is completed, the magnet assembly can be removed from the abdominal cavity of the patient. The method for removing the magnet assembly can vary depending on the design of the partitioning device. The magnet assembly can be removed from the target hollow organ and the abdominal cavity laparoscopically by pulling one of the leading elongated member and the trailing elongated member out of the patient, optionally with a delivery catheter. The magnet assembly can also be removed from the target hollow organ and the abdominal cavity laparoscopically by pulling directly the magnet assembly out of the patient, also optionally with a delivery catheter. In some implementations, the magnet assembly can be removed during an open surgery. Again, various techniques can be used to remove the magnet assembly from the abdominal cavity of the patient, which may be the same or different as the technique used previously to insert and place the magnet assembly round the target hollow organ, and can include laparoscopic surgery, open surgery, image-guided procedures and flexible endoscopy, for instance.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A partitioning device to partition a hollow organ of a digestive tract of a patient, the partitioning device comprising:
   a magnet assembly implantable into an abdominal cavity of the patient and comprising:
      a plurality of magnet elements flexibly connected in series;
   wherein the magnet assembly is configured to be positioned extraluminally around at least a portion of an outer surface of the hollow organ to magnetically couple opposite magnet elements together to compress opposite walls of the hollow organ therebetween and subject the opposite walls of the hollow organ to ischemic pressure necrosis to fuse the opposite walls of the hollow organ together, thereby partitioning the hollow organ.

2. The partitioning device of claim 1, further comprising a leading elongated member and a trailing elongated member, with the magnet assembly extending therebetween.

3. The partitioning device of claim 2, wherein the leading elongated member is configured for engagement with a delivery catheter to guide the magnet assembly to the hollow organ and around the at least a portion of the outer surface thereof.

4. The partitioning device of claim 2, wherein each one of the magnet elements comprises a magnet-engaging side to magnetically couple opposite magnet-engaging sides of the magnet elements facing each other.

5. The partitioning device of claim 4, wherein the magnet-engaging side of the magnet elements have a smaller surface area compared to a side of the magnet element located opposite the magnet-engaging side.

6. The partitioning device of claim 4, wherein the magnet assembly comprises a first zone and a second zone, the magnet-engaging sides of the magnet elements of the first zone of the magnet assembly having a first zone magnetic pole, and the magnet-engaging sides of the magnet elements of the second zone of the magnet assembly having a second zone magnetic pole that is different from the first zone magnetic pole.

7. The partitioning device of claim 6, wherein the partitioning device comprises a curved region extending between the first zone and the second zone.

8. The partitioning device of claim 2, wherein the magnet elements have a shape selected from the group consisting of an oblong shape, a stadium shape, a circular shape, a triangular shape, a rectangular shape, an octagonal shape and combinations thereof.

9. The partitioning device of claim 2, wherein the magnet elements comprise bevelled edges.

10. The partitioning device of claim 2, wherein the magnet elements comprise rounded edges.

11. The partitioning device of claim 2, wherein the magnet elements are flexibly connected in series via a flexible connector.

12. The partitioning device of claim 11, wherein the flexible connector comprises a flexible string.

13. The partitioning device of claim 2, wherein the partitioning device is configurable between a pre-partitioning configuration and a partitioning configuration.

14. The partitioning device of claim 2, wherein an attractive force of the magnet element is determined at least in part in accordance with a thickness and/or a composition of the hollow organ.

15. The partitioning device of claim 2, wherein an attractive force of the magnet elements is determined so as to facilitate placement and implantation of the partitioning device around the portion of the outer surface of the hollow organ.

16. The partitioning device of claim 2, wherein the plurality of magnet elements flexibly connected in series are provided in sufficiently close proximity to enable formation of a substantially continuous partition line once the opposite walls of the hollow organ are fused together.

17. The partitioning device of claim 2, wherein the magnet elements are received in a housing.

18. The partitioning device of claim 17, wherein the housing comprises bevelled edges.

19. The partitioning device of claim 2, wherein each one the magnet elements is received in a corresponding housing.

20. The partitioning device of claim 19, wherein the corresponding housing comprises bevelled edges.

* * * * *